United States Patent [19]

Buchecker et al.

[11] Patent Number: 5,667,721
[45] Date of Patent: Sep. 16, 1997

[54] LIQUID CRYSTALLINE DI-1,3-DIOXANE DERIVATIVES

[75] Inventors: Richard Buchecker, Zurich, Switzerland; Guy Marck, Rixheim, France; Alois Villiger, Basel, Switzerland

[73] Assignee: Rolic AG, Basel, Switzerland

[21] Appl. No.: 604,630

[22] Filed: Feb. 21, 1996

[30] Foreign Application Priority Data

Mar. 16, 1995 [CH] Switzerland ................ 754/95

[51] Int. Cl.$^6$ .............. C09K 19/34; C09K 19/30; C07D 407/04; C07D 407/06
[52] U.S. Cl. ............... 252/299.61; 549/370; 546/256; 546/282.4; 544/296; 544/318; 544/333; 544/335
[58] Field of Search ............ 549/370; 546/256, 546/282.4; 544/296, 318, 333, 335; 252/299.61

[56] References Cited

U.S. PATENT DOCUMENTS 5,322,638  6/1994  Schadt et al. .

FOREIGN PATENT DOCUMENTS

| 0 087 679 | 2/1983 | European Pat. Off. . |
| 0 433 836 | 10/1990 | European Pat. Off. . |
| 2 105 717 | 8/1982 | United Kingdom . |
| 91 11497 | 8/1991 | WIPO . |

OTHER PUBLICATIONS

Patent Abstracts of Japan, vol. 18 No. 668, 1994.
Derwent Abstract corresponding to EP 0 087 679, #83-760075/37, 1983.
Abstract corresponding to WO 91 11497, 1991.

*Primary Examiner*—Nicky Chan
*Attorney, Agent, or Firm*—George W. Johnston; Ellen Ciambrone Coletti; Robert A. Silverman

[57] ABSTRACT

Liquid crystalline compounds having two dioxane rings, the dipole moments of which are unidirectional. These are compounds of the general formula

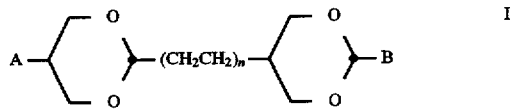

wherein
A and B each independently is cyclic or acyclic hydrophobic residues; and
n is 0, 1 or 2.

as well as liquid crystalline mixtures which contain such compounds and the use of such compounds and, respectively, mixtures for electro-optical display devices.

21 Claims, No Drawings

LIQUID CRYSTALLINE DI-1,3-DIOXANE DERIVATIVES

FIELD OF THE INVENTION

The present invention is concerned with liquid crystalline compounds having two 1,3-dioxane rings, the dipole moments of which are unidirectional. The invention is also concerned with liquid crystalline mixtures containing such di-dioxane derivatives and with the use of such compounds and mixtures in electro-optical devices.

BACKGROUND

Liquid crystals are used primarily as dielectrics in display devices, since the optical properties of such substances can be influenced by an applied voltage. Electro-optical devices based on liquid crystals are well-known and can be based on various effects. Such devices are, for example, cells having dynamic scattering, DAP cells (deformation of aligned phases), guest/host cells, TN cells having a "twisted nematic" structure, STN cells ("super twisted nematic"), SBE cells ("super birefringence effect") and OMI cells ("optical mode interference"). For displays having a high content of information, actively controlled cells, e.g. TFT cells ("thin film transistor"), have in particular recently become important in addition to passively controlled, multiplexed cells. The most common display devices are based on the Schadt-Helfrich effect and have a twisted nematic structure.

The liquid crystal materials must have a good chemical, photochemical and thermal stability and a good stability towards electric fields. Further, they should have a suitable mesophase over a range which is as broad as possible (for example, a nematic or a cholesteric phase for the cells referred to above), but in spite of a sufficiently low viscosity should permit short response times, low threshold potentials and a high contrast in the cells. Further properties such as the electrical conductivity, the dielectric anisotropy and the optical anisotropy must fulfil different requirements depending on the field of application and type of cell. For example, materials for cells having a twisted nematic structure should have a positive dielectric anisotropy which is as high as possible and at the same time should have a conductivity which is as low as possible. The latter property is of particular importance primarily for actively addressed liquid crystal displays having a high density of information, e.g. TFT cells. Unfortunately, however, components having a high dielectric anisotropy mainly lead to an increased conductivity in mixtures because of their improved capacity to dissolve ionic impurities. Accordingly, components which are distinguished by a dielectric anisotropy which is as high as possible with simultaneously a conductivity which is as low as possible are sought after.

SUMMARY OF THE INVENTION

The present invention is concerned with a compound of the formula

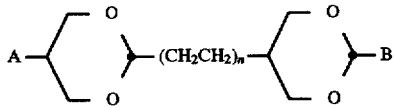

wherein
A and B each independently are cyclic or acyclic hydrophobic residues; and
n is 0, 1 or 2.

The liquid crystalline compounds of the present invention have a very high dielectric anisotropy ($\Delta\epsilon$) and an extraordinarily low conductivity. Moreover, these compounds are surprisingly stable and are suitable also with respect to the other properties as components for liquid crystal mixtures.

The liquid crystalline compounds in accordance with the invention have an extraordinarily low optical anisotropy ($\Delta n$). Also, their electric anisotropy ($\Delta\epsilon$) is distinctly higher than in known compounds which have the same end groups and comparable low optical anisotropy. Moreover, the compounds in accordance with the invention have a good chemical and photochemical stability and are soluble in liquid crystal mixtures without influencing the viscosity and the mesophase of these mixtures. The $S_B$ mesophase which occurs in the case of these compounds can be readily suppressed in nematic mixtures. In contrast to previously known compounds having a high dielectric anisotropy, the compounds in accordance with the invention have a very low electrical conductivity. These properties mean that the use of such compounds leads to mixtures having a very low threshold potential ($V_{10}$), low optical anisotropy and broad nematic phases. They are accordingly particularly suitable for use in TN cells (operated in the 1st minimum), OMI cells and STN cells and primarily also for use in actively addressed display devices.

DETAILED DESCRIPTION OF THE INVENTION

The term "cyclic or acyclic hydrophobic residues" for A and B are residues such as
—$R^1$,

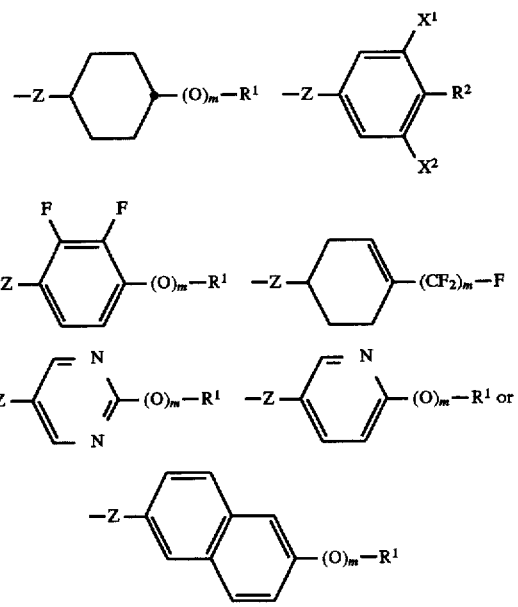

wherein
Z is a single bond, —$CH_2CH_2$— or —$(CH_2)_4$—;
$X^1$ and $X^2$ each independently are hydrogen or fluorine;
m is 0 or 1;
$R^1$ is alkyl, alkenyl, or alkoxyalkyl which is unsubstituted or substituted with at least one fluorine or chlorine atom; and
$R^2$ is $R^1$, —O—$R^1$, fluorine, chlorine, cyano or isothiocyanato.

"Alkyl" is straight-chain or branched, optionally chiral residues with 1 to 12 carbon atoms. Examples of such residues are methyl, ethyl, propyl, butyl, pentyl, hexyl, heptyl, isopropyl, 2-methyl-butyl, 2-methyl-pentyl, 2-methyl-hexyl, 3-methyl-butyl, 3-methyl-pentyl, 3-methyl-hexyl, 4-methyl-methyl-hexyl and 5-methyl-hexyl.

"Alkoxyalkyl" is straight-chain or branched, optionally chiral residues with 2 to 12 carbon atoms. Examples of such residues are methoxymethyl, 2-methoxyethyl, 3-methoxypropyl, 4-methoxybutyl, 5-methoxypentyl, ethoxymethyl, 2-ethoxyethyl, 3-ethoxypropyl, 4-ethoxybutyl, propyloxymethyl, 2-propyloxyethyl, 8-propyloxypropyl, butyloxymethyl and 2-butyloxyethyl.

"Alkenyl" is straight-chain or branched, optionally chiral residues with 2 to 12 carbon atoms in which the double bond is either in the 1-, 2-, 3- or 4-position or is terminal. Examples of such residues are 1E-alkenyl such as 1E-propenyl, 1E-butenyl, 1E-pentenyl, 1E-hexenyl and 1E-heptenyl; 2E-alkenyl such as 2E-butenyl, 2E-pentenyl, 2E-hexenyl and 2E-heptenyl; 3E-alkenyl such as 3E-pentenyl, 3E-hexenyl and 3E-heptenyl; 4-alkenyl such as 4-hexenyl, 4-heptenyl; or alkenyl with a terminal double bond such as vinyl, allyl, 3-butenyl, 4-pentenyl, 5-hexenyl and 6-heptenyl.

In the term "alkyl, alkenyl or alkoxyalkyl which is unsubstituted or substituted with at least one fluorine or chlorine atom", these residues can be substituted with one or more fluorine and/or chlorine atom. Such substituted residues are, for example, fluoromethyl, difluoro-methyl, trifluoromethyl, chloro-difluoromethyl, 2-fluoroethyl, 2,2-difluoroethyl, 2,2,2-trifluoroethyl, perfluoroethyl, perfluoro-propyl, E-chlorovinyl, E-fluorovinyl, 2,2-difluorovinyl and the like.

Straight-chain alkyl, alkenyl or alkoxyalkyl residues with 1 or, respectively, 2 to 7 carbon atoms are especially preferred.

Propyl, butyl, pentyl, difluoromethyl, trifluoromethyl, vinyl, E-propenyl, 1E-butenyl, 1E-pentenyl, 3-butenyl, 3E-pentenyl, E-fluorovinyl, 2,2-difluorovinyl or E-chlorovinyl are especially preferred residues $R^1$.

Preferred compounds of formula I are those of the formulas

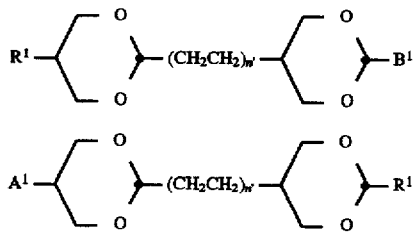

I-A

I-B wherein n' is 0 or 1;

$R^1$ is as described above;

$A^1$ is alkyl, alkenyl, alkoxyalkyl or a group of the formula

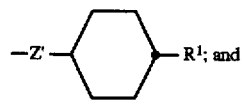

$B^1$ is alkyl, alkenyl, alkoxyalkyl or a group of the formula

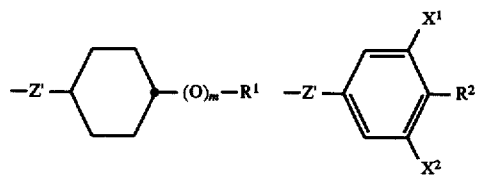

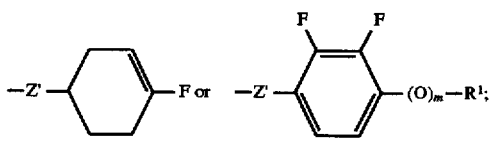

wherein m is 0 or 1;

Z' is a single bond or —$CH_2CH_2$—;

$R^1$ is as described above;

$R_2$ is as described above; and $X^1$, $X^2$ are as described above.

Especially preferred compounds of formula I-A are compounds of the formulas

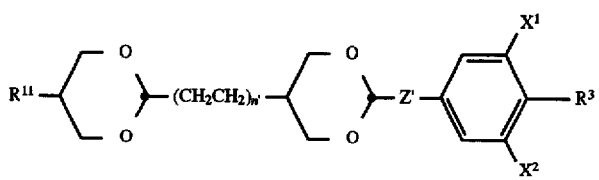

I-A1

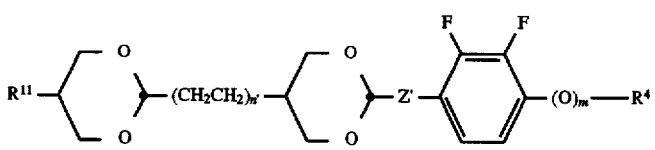

I-A2

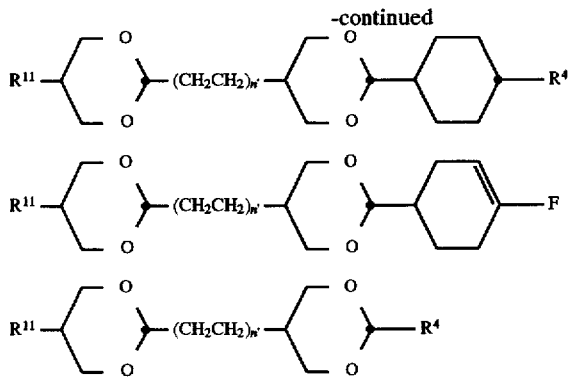

I-A3

I-A4

I-A5 wherein $R^{11}$ is $C_1$–$C_7$ alkyl or $C_2$–$C_7$ alkenyl;

n' is 0 or 1;

m is 0 or 1;

$X^1$ and $X^2$ are as described above;

Z' is a single bond or —$CH_2CH_2$—;

$R^3$ is alkoxy, difluoromethoxy, trifluoromethoxy, chlorodifluoromethoxy, 2,2,2-trifluoroethyloxy, fluorine, chlorine or cyano; and $R^4$ is $C_1$–$C_7$ alkyl, $C_2$–$C_7$ alkoxyalkyl or $C_2$–$C_7$ alkenyl.

Especially preferred compounds of formula I-B are

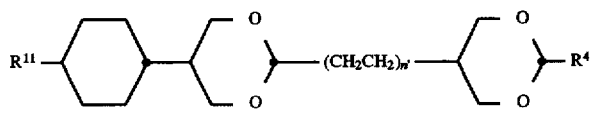

I-B1

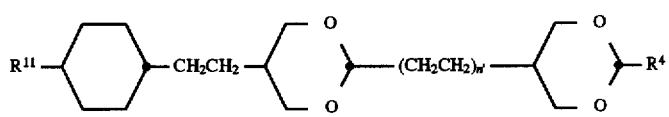

I-B2 wherein $R^{11}$, n' and $R^4$ are as described above.

The compounds of formula I in accordance with the invention can be produced in a known manner. The synthesis is illustrated in Scheme 1. Thus, 2,5'-bi-1,3-dioxanes of formula I in which n=0 can be produced starting from an alkoxymethylidene-malonic ester (2b) and a correspondingly substituted 1,3-propanediol (1) via a dioxanylmalonic ester (5, n=0). The reaction of the alkoxymethylidene-malonic ester (2b) with the 1,3-propanediol (1) can be effected, for example, in an inert solvent in the presence of a catalytic amount of an acid such as p-toluenesulphonic acid (TsOH). The alkoxymethylidene-malonic esters (2b) and the 1,3-propanediols (1) are known or can be prepared by known methods.

Di-1,3-dioxane derivatives of formula I in which n=1 or 2 can be produced via the intermediate 3, in which n=1 or 2, for example by trans-acetalization of a correspondingly substituted bromoalkyldioxolane (2a) to the dioxane (3) (as a cis/trans mixture), which can be converted into the malonic ester (5, n=1 or 2) by subsequent alkylation of an alkali salt of dialkyl malonate (4). The substituted bromoalkyldioxolanes (2a) and alkali salts of dialkyl malonate (4) are known or can be prepared by known methods. The intermediates 5 (not only n=0 but also n=1 or 2) can be reduced in an inert solvent, for example with lithium aluminium hydride, to the corresponding diols (6), with the working up preferably being effected in basic medium. In the final step, these diols (6) can be reacted with correspondingly substituted aldehydes (7) in an inert solvent at about 50°–110° C. and in the presence of an acidic catalyst (for example, p-toluenesulfonic acid, dilute sulfuric acid or pyridinium p-toluenesulfonate). The substituted aldehydes (7) are known or can be prepared by known methods. For compounds of formula I in which Z signifies —$CH_2CH_2$—, the diols (6) can be reacted with corresponding derivatives of the aldehydes (7), for example an enol ether or an acetal. The reaction time and the acid concentration are critical because on the one hand of the possible opening of the dioxane ring of the diol (6) and because on the other hand on the achievement of the equilibrium which is required for high yields of all-trans compounds. The all-trans isomers of formula I can be isolated by chromatography of the mixture of isomers and subsequent recrystallization.

Scheme 1

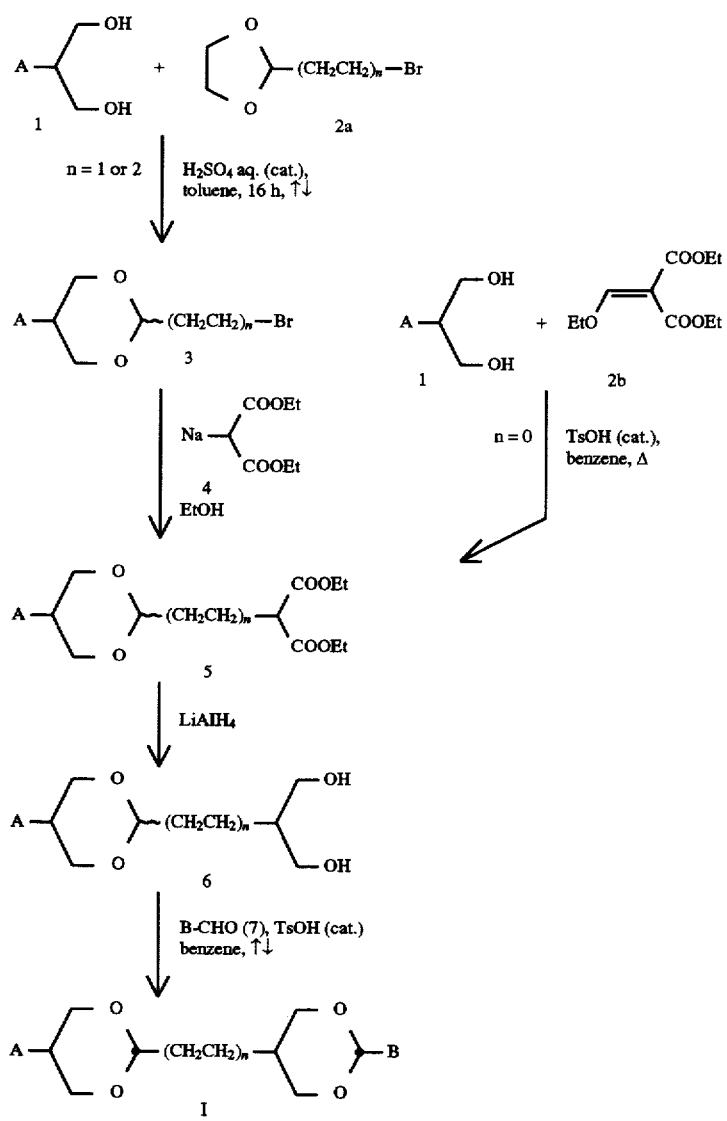

A, B and n are as described above.

The compounds of formula I can be used in the form of mixtures with one another and/or with other liquid crystal components. Other suitable liquid crystal components are known for example, from D. Demus et al., Flüssige Kristalle in Tabellen, VEB Deutscher Verlag für Grundstoffindustrie, Leipzig, Volumes I and II, and, moreover, many are commercially available.

The invention is also concerned with liquid crystalline mixtures having at least 2 components, with at least one component being a compound of formula I. A second component and optionally additional components can be further compounds of formula I or other suitable liquid crystal components.

Having regard to the good solubility of the compounds of formula I in other liquid crystal materials and having regard to their good miscibility with one another, the content of compounds of formula I in the mixtures in accordance with the invention can be relatively high and can be, for example, 1–30 wt. %. In general, a content of about 1–25 wt. %, especially of about 3–20 wt. %, of compounds of formula I is preferred.

Preferably, the mixtures in accordance with the invention contain, in addition to one or more compounds of formula I, one or more compounds from the group of compounds of the formulas

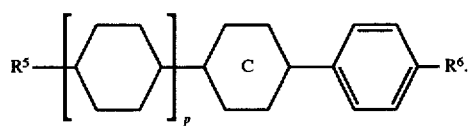 II
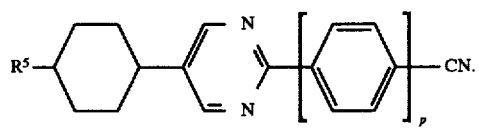 III
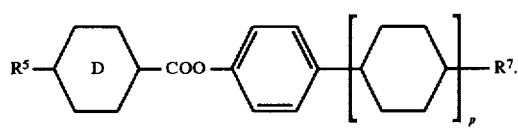 IV
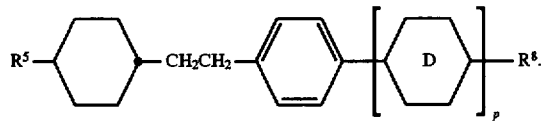 V
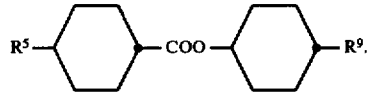 VI
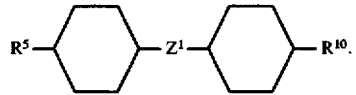 VII
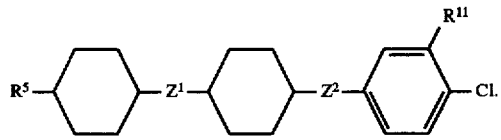 VIII
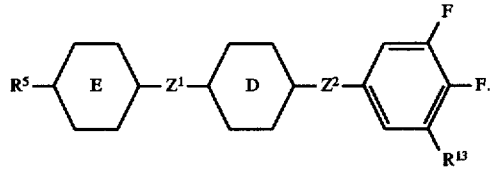 IX
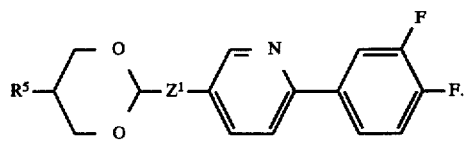 X
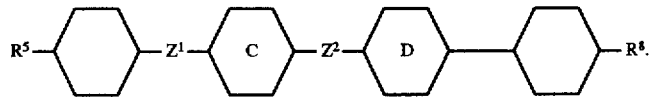 XI
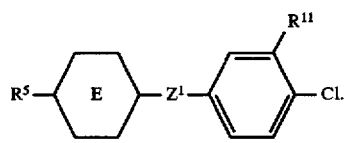 XII
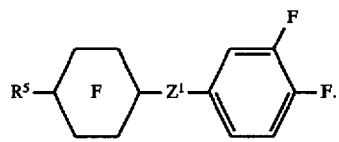 XIII

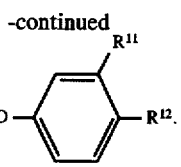

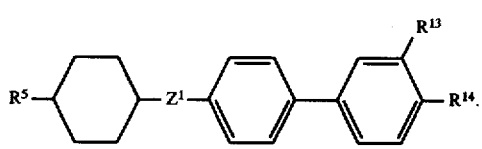

and

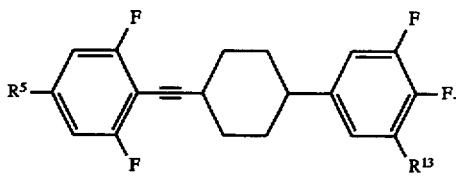

wherein $R^5$, $R^7$ each independently are alkyl, alkoxyalkyl, 3E-alkenyl, 4-alkenyl or on saturated rings also 1E-alkenyl;

is 0 or 1;

ring C is 1,4-phenylene, pyridine-2,5-diyl, pyrimidine-2,5-diyl, trans-1,4-cyclohexylene or trans-1,3-dioxane-2,5-diyl;

$R^6$ is cyano, isothiocyanato, fluorine, alkyl, 3E-alkenyl, 4-alkenyl, alkoxy, 2E-alkenyloxy, 3-alkenyloxy or 1-alkynyl;

ring D is 1,4-phenylene or trans-1,4-cyclohexylene;

$R^8$ is alkyl, 3E-alkenyl, 4-alkenyl or on trans-1,4-cyclohexylene also 1E-alkenyl or on 1,4-phenylene also cyano, isothiocyanato, alkoxy, 2E-alkenyloxy or 3-alkenyloxy;

$R^9$ is alkyl, 1E-alkenyl, 3E-alkenyl or 4-alkenyl;

R10 is cyano, alkyl, 1E-alkenyl, 3E-alkenyl, 4-alkenyl, alkoxy, 2E-alkenyloxy, 3-alkenyloxy, alkoxymethyl or (2E-alkenyl)oxymethyl;

$Z^1$, $Z^2$ each independently are a single covalent bond or —$CH_2CH_2$—, with two aromatic rings always being linked by a single covalent bond;

ring E is trans-1,4-cyclohexylene or trans-1,3-dioxane-2,5-diyl;

$R^{11}$ is hydrogen, fluorine or chlorine;

$R^{12}$ is cyano, fluorine or chlorine;

$R^{13}$ is hydrogen or fluorine;

$R^{14}$ is fluorine or chlorine; and ring F is pyrimidine-2,5-diyl, trans-1,4-cyclohexylene or trans-1,3-dioxane-2,5-diyl.

The terms used in connection with the compounds of formulae II to XVI are as defined in more detail hereinbefore. The term "aromatic rings" denotes rings such as, for example, 1,4-phenylene, pyridine-2,5-diyl or pyrimidine-2,5-diyl. The term "saturated rings" denotes trans-1,4-cyclohexylene or trans-1,3-dioxane-2,5-diyl.

The term "alkoxy" signifies straight-chain or branched, optionally chiral residues with 1 to 12 carbon atoms, preferably straight-chain residues such as, for example, methoxy, ethoxy, propyloxy, butyloxy, pentyloxy, hexyloxy, heptyloxy and the like. "2E- or 3-Alkenyloxy" signifies in this connection preferably straight-chain alkenyloxy residues with 3 or 4 to 12 carbon atoms in which the double bond is situated in the 2- or 3-position and E or Z indicates the preferred configuration, such as, for example, allyloxy, 2E-butenyloxy, 2E-pentenyloxy, 2E-hexenyloxy, 2E-heptenyloxy, 3-butenyloxy, 3-pentenyloxy, 3-hexenyloxy, 3-heptenyloxy, 4-pentenyloxy, 5-hexenyloxy, 6-heptenyloxy and the like.

"1-Alkynyl" signifies in this connection preferably straight-chain alkynyl residues with 2 to 12 carbon atoms in which the triple bond is situated in the 1-position, such as, for example, ethynyl, 1-propynyl, 1-butynyl, 1-pentynyl and the like.

The mixtures in accordance with the invention can also contain optically active compounds (for example, optically active 4'-alkyl- or 4'-alkoxy-4-biphenylcarbonitriles) and/or dichroic dyes (for example, azo, azoxy or anthraquinone dyes). The content of such compounds is determined by the solubility, the desired helical pitch, colour, extinction and the like. In general, the content of optically active compounds and dichroic dyes is a maximum of in each case about 10 wt. % in the final mixture.

The production of the liquid crystalline mixtures and of the electro-optical devices can be effected in a known manner.

The production of the compounds of formula I and of liquid crystalline mixtures containing these compounds is illustrated in more detail by the following Examples. C signifies a crystalline phase, S signifies a smectic phase, N signifies the nematic phase and the I signifies the isotropic phase. $V_{10}$ denotes the voltage for 10% transmission (viewing direction perpendicular to the plate surface). $t_{on}$ and $t_{off}$ denote, respectively, the switching-on time and the switching-off time. $\Delta n$ denotes the optical anisotropy and GC signifies gas chromatography.

EXAMPLE 1

A solution of 1.50 g of (E)-2-[2-(5-but-1-enyl-1,3-dioxan-2-yl)ethyl]-1,3-propanediol and 2 ml of butyraldehyde in 40 ml of benzene was treated with 28.5 mg of p-toluenesulfonic acid monohydrate and stirred at 68° C. for 40 minutes. The reaction mixture was neutralized with a few drops of triethylamine and, after cooling, washed with saturated sodium chloride solution, dried over sodium sulfate and concentrated. The crude product (2.15 g) was chromatographed on 40 g of silica gel with hexane/ethyl acetate 5% (v/v). 1.40 g of isomer mixture having a 52% trans/trans content were obtained. Two-fold recrystallization from hexane gave 0.41 g of pure (E)-trans-2-propyl-5-[2-(trans-5-but-1-enyl-1,3-dioxan-2-yl)ethyl]-1,3-dioxane, m.p. (C-S$_B$) 42° C., cl.p. (S$_B$-I) 117.8° C.

The (E)-2-[2-(5-but-1-enyl-1,3-dioxan-2-yl)-ethyl]-1,3-propanediol used as the starting material was prepared as follows:

a) A solution of 14.4 ml of 2-(2-bromoethyl)-dioxolane and 20.6 g of (E)-2-but-1-enyl-1,3-propanediol in 200 ml of toluene was heated to slight boiling overnight with 2.7 ml of 10% aqueous sulfuric acid (v/v) and 8 ml of water. The mixture was treated with 6 ml of triethylamine and the aqueous phase was separated. The organic phase was washed with semi-conc. sodium chloride solution, dried over sodium sulfate, filtered and concentrated. The resulting orange oil (31.3 g) was chromatographed on 400 g of silica gel with hexane/ethyl acetate 2.5% (v/v). 23.4 g of (E)-2-(2-bromoethyl)-5-but-1-enyl-1,3-dioxane (GC purity 97.5%, trans/cis ratio 73:27) were obtained as a yellowish oil.

b) A sodium ethylate solution, freshly prepared from 2.3 g of sodium in 60 ml of ethanol, was added dropwise to a solution of 13.0 ml of diethyl malonate in 40 ml of ethanol and, after stirring for 45 minutes, 23.4 g of (E)-2-(2-bromoethyl)-5-but-1-enyl-1,3-dioxane were added dropwise. The reaction mixture was left to stand overnight and then heated to boiling for 30 minutes. After cooling the mixture was firstly diluted with 150 ml of diethyl ether and washed with 100 ml of semi-concentrated sodium chloride solution and then with 50 ml of concentrated sodium chloride solution, dried over sodium sulfate, filtered and concentrated. The resulting orange-red oil (29.5 g) was separated by chromatography on 300 g of silica gel with hexane/ethyl acetate 5% (v/v). The product-containing fractions (24.0 g) were distilled in order to separate the dialkylated byproducts. The fraction with b.p. 130°–150° /about 0.01 Torr weighed 16.75 g and according to GC consisted to 95% of a trans/cis mixture of diethyl (E)-[2-(5-but-1-enyl-1,3-dioxan-2-yl-ethyl]-malonate.

c) A solution of 16.75 g of diethyl (E)-[2-(5-but-1-enyl-1,3-dioxan-2-yl)-ethyl]-malonate in 25 ml of tetrahydrofuran was added dropwise at 5°–8° C. under a protective gas to a suspension of 3.87 g of lithium aluminium hydride in 100 ml of tetrahydrofuran. The reaction mixture was stirred at 5° C. for a further 15 minutes, then at room temperature for 2 hours and finally at the boiling temperature for 1.2 hours. After cooling 3N sodium hydroxide solution was cautiously added dropwise until a solid white clump formed. The solution was decanted and the residue was washed twice with diethyl ether. The organic phases were combined, washed in succession with 25 ml of concentrated sodium bicarbonate solution and twice with 25 ml of concentrated sodium chloride solution each time, dried over sodium sulfate, filtered and the filtrate was concentrated. 12.20 g of crude (E)-2-[2-(5-but-1-enyl-1,3-dioxan-2-yl)-ethyl]-1,3-propanediol were obtained as a sticky-solid crude product, m.p. up to 87.1° C. (GC purity 86%, trans/cis ratio 7:3), which was used in the final step without further purification.

In an analogous manner there can be prepared:

trans-2-ethyl-5-[2-(trans-5-propyl-1,3-dioxan-2-yl)-ethyl]-1,3-dioxane, m.p. (C-S$_B$) 56.8° C., cl.p. (S$_B$-I) 75.1° C.;

trans-2-ethyl-5-[2-(trans-5-butyl-1,3-dioxan-2-yl)-ethyl]-1,3-dioxane;

trans-2-ethyl-5-[2-(trans-5-pentyl-1,3-dioxan-2-yl)-ethyl]-1,3-dioxane, m.p. (C-S$_B$) 40.0° C., cl.p. (S$_B$-I) 91° C.;

(E)-trans-2-ethyl-5-[2-(trans-5-propenyl-1,3-dioxan-2-yl)-ethyl]-1,3-dioxane, m.p. (C-S$_B$) 68° C., cl.p. (S$_B$-I) 76.6° C.;

trans-2-propyl-5-[2-(trans-5-propyl-1,3-dioxan-2-yl)-ethyl]-1,3-dioxane, m.p. (C-S$_B$) 58° C., cl.p. (S$_B$-I) 98.3° C.;

trans-2-propyl-5-[2-(trans-5-butyl-1,3-dioxan-2-yl)-ethyl]-1,3-dioxane, m.p. (C-S$_B$) 62.5° C., cl.p. (S$_B$-I) 110° C.;

trans-2-propyl-5-[2-(trans-5-pentyl-1,3-dioxan-2-yl)-ethyl]-1,3-dioxane, m.p. (C-S$_B$) 57.5° C., cl.p. (S$_B$-I) 113.1° C.;

trans-2-propyl-5-[2-(trans-5-hexyl-1,3-dioxan-2-yl)-ethyl]-1,3-dioxane;

(E)-trans-2-propyl-5-[2-(trans-5-propenyl-1,3-dioxan-2-yl)-ethyl]-1,3-dioxane, m.p. (C-S$_B$) 68.7° C., cl.p. (S$_B$-I) 100.5° C.;

(E)-trans-2-propyl-5-[2-(trans-5-pent-1-enyl-1,3-dioxan-2yl)-ethyl]-1,3-dioxane;

trans-2-propyl-5-[trans-5-but-3-enyl-1,3-dioxan-2-yl)-ethyl]-1,3-dioxane;

trans-2-propyl-5-[trans-5-(3-methoxy-propyl)-1,3-dioxan-2-yl]-1,3-dioxane;

trans-2-butyl-5-[trans-5-propyl-1,3-dioxan-2-yl)-1,3-dioxane, m.p. (C-S$_B$) 61.5° C., cl.p. (S$_B$-I) 102.8° C.

trans-2-butyl-5-(trans-5-butyl-1,3-dioxan-2-yl)-1,3-dioxane, m.p. (C-S$_B$) 78.5° C., cl.p. (S$_B$-I) 112° C.;

trans-2-butyl-5-(trans-5-pentyl-1,3-dioxan-2-yl)-1,3-dioxane, m.p. (C-S$_B$) 65° C., cl.p. (S$_B$-I) 116.3° C.;

(E)-trans-2-butyl-5-(trans-5-propenyl-1,3-dioxan-2-yl)-1,3-dioxane, m.p. (C-S$_B$) 45.5° C., cl.p. (S$_B$-I) 106.8° C.;

(E)-trans-2-butyl-5-(trans-5-but-1-enyl-1,3-dioxan-2-yl)-1,3-dioxane, m.p. (C-S$_B$) 42° C, cl.p. (S$_B$-I) 120.5° C.;

(E)-trans-2-butyl-5-(trans-5-pent-1-enyl-1,3-dioxan-2-yl)-1,3-dioxane;

trans-2-pentyl-5-(trans-5-propyl-1,3-dioxan-2-yl)-1,3-dioxane;

trans-2-pentyl-5-(trans-5-butyl-1,3-dioxan-2-yl)-1,3-dioxane;

trans-2-pentyl-5-[2-(trans-5-pentyl-1,3-dioxan-2-yl)-ethyl]-1,3-dioxane;

(E)-trans-2-pentyl-5-[2-(trans-5-but-1-enyl-1,3-dioxan-2-yl)-ethyl]-1,3-dioxane;

(E)-trans-2-pentyl-5-[2-(trans-5-pent-1-enyl-1,3-dioxan-2-yl)-ethyl]-1,3-dioxane;

trans-2-pentyl-5-[2-(trans-5-but-3-enyl-1,3-dioxan-2-yl)-ethyl]-1,3-dioxane;

(E)-trans-2-pentyl-5-[2-(trans-5-pent-3-enyl-1,3-dioxan-2-yl)-ethyl]-1,3-dioxane;

trans-2-pentyl-5-[2-(trans-5-pent-4-enyl-1,3-dioxan-2-yl)-ethyl]-1,3-dioxane;

trans-2-pentyl-5-[2-[trans-5-(3-methoxy-propyl)-1,3-dioxan-2-yl]-ethyl]-1,3-dioxane;

trans-2-(trans-4-ethylcyclohexyl)-5-[2-(trans-5-propyl-1,3-dioxan-2-yl)-ethyl]-1,3-dioxane;

trans-2-(trans-4-ethylcyclohexyl)-5-[2-(trans-5-pentyl-1,3-dioxan-2-yl)-ethyl]-1,3-dioxane;

trans-2-(trans-4-propylcyclohexyl)-5-[2-(trans-5-propyl-1,3-dioxan-2-yl)-ethyl]-1,3-dioxane;

trans-2-(trans-4-propylcyclohexyl)-5-[2-(trans-5-butyl-1,3-dioxan-2-yl)-ethyl]-1,3-dioxane;

trans-2-(trans-4-propylcyclohexyl)-5-[2-(trans-5-pentyl-1,3-dioxan-2-yl)-ethyl]-1,3-dioxane;

(E)-trans-2-(trans-4-propylcyclohexyl)-5-[2-(trans-5-propenyl-1,3-dioxan-2-yl)-ethyl]-1,3-dioxane;

(E)-trans-2-(trans-4-propylcyclohexyl)-5-[2-(trans-5-but-1-enyl-1,3-dioxan-2-yl)-ethyl]-1,3-dioxane;

(E)-trans-2-(trans-4-propylcyclohexyl)-5-[2-(trans-5-pent-1-enyl-1,3-dioxan-2-yl)-ethyl]-1,3-dioxane;

trans-2-(trans-4-butylcyclohexyl)-5-[2-(trans-5-propyl-1,3-dioxan-2-yl)-ethyl]-1,3-dioxane, m.p. (C-$S_B$) 107° C., cl.p. ($S_B$-I) 168.5° C.;

trans-2-(trans-4-butylcyclohexyl)-5-[2-trans-5-butyl-1,3-dioxan-2-yl)-ethyl]-1,3-dioxane, m.p. (C-$S_B$) 100° C., cl.p. ($S_B$-I) 177° C.;

trans-2-(trans-4-butylcyclohexyl)-5-[2-(trans-5-pentyl-1,3-dioxan-2-yl)-ethyl]-1,3-dioxane, m.p. (C-$S_B$) 105° C., cl.p. ($S_B$-I) 184° C.;

(E)-trans-2-(trans-4-butylcyclohexyl)-5-[2-(trans-5-propenyl-1,3-dioxan-2-yl)-ethyl]-1,3-dioxane, m.p. (C-$S_B$) 117.5° C., cl.p. ($S_B$-I) 181.5° C.;

(E)-trans-2-(trans-4-butylcyclohexyl)-5-[2-(trans-5-but-1-enyl-1,3-dioxan-2-yl)-ethyl]-1,3-dioxane, m.p. (C-$S_B$) 105° C., cl.p. ($S_B$-I) 191.5° C.;

(E)-trans-2-(trans-4-butylcyclohexyl)-5-[2-(trans-5-pent-1-enyl-1,3-dioxan-2-yl)-ethyl]-1,3-dioxane;

trans-2-(trans-4-butylcyclohexyl)-5-[2-(trans-5-but-3-enyl-1,3-dioxan-2-yl)-ethyl]-1,3-dioxane;

trans-2-(trans-4-pentylcyclohexyl)-5-[2-(trans-5-propyl-1,3-dioxan-2-yl)-ethyl]-1,3-dioxane;

trans-2-(trans-4-pentylcyclohexyl)-5-[2-(trans-5-pentyl-1,3-dioxan-2-yl)-ethyl]-1,3-dioxane;

(E)-trans-2-(trans-4-pentylcyclohexyl)-5-[2-(trans-5-propenyl-1,3-dioxan-2-yl)-ethyl]-1,3-dioxane;

(E)-trans-2-(trans-4-pentylcyclohexyl)-5-[2-(trans-5-but-1-enyl-1,3-dioxan-2-yl)-ethyl]-1,3-dioxane;

trans-2-(4-fluorophenyl)-5-[2-(trans-5-propyl-1,3-dioxan-2-yl)-ethyl]-1,3-dioxane;

trans-2-(4-fluorophenyl)-5-[2-(trans-5-butyl-1,3-dioxane-2-yl)-ethyl]-1,3-dioxane;

trans-2-(4-fluorophenyl)-5-[2-(trans-5-pentyl-1,3-dioxan-2-yl)-ethyl]-1,3-dioxane;

(E)-trans-2-(4-fluorophenyl)-5-[2-(trans-5-propenyl-1,3-dioxan-2-yl)-ethyl]-1,3-dioxane;

(E)-trans-2-(4-fluorophenyl)-5-[2-(trans-5-but-1-enyl-1,3-dioxan-2-yl)-ethyl]-1,3-dioxane;

trans-(4-chlorophenyl)-5-[2-(trans-5-propyl-1,3-dioxan-2-yl)-ethyl]-1,3-dioxane;

trans-(4-chlorophenyl)-5-[2-(trans-5-butyl-1,3-dioxane-2-yl)-ethyl]- 1,3-dioxane;

trans-(4-chlorophenyl)-5-[2-(trans-5-pentyl-1,3-dioxan-2-yl)-ethyl]-1,3-dioxane;

(E)-trans-(4-chlorophenyl)-5-[2-(trans-5-propenyl-1,3-dioxan-2-yl)ethyl]-1,3-dioxane;

(E)-trans-(4-chlorophenyl)-5-[2-(trans-5-but-1-enyl-1,3-dioxan-2-yl)-ethyl]-1,3-dioxane;

(E)-trans-(4-chlorophenyl)-5-[2-(trans-5-pent-1-enyl-1,3-dioxan-2-yl)-ethyl]-1,3-dioxane;

trans-2-(4-trifluoromethyl-phenyl)-5-[2-(trans-5-propyl-1,3-dioxan-2yl)-ethyl]-1,3-dioxane, m.p. (C-$S_B$) 124° C., cl.p. ($S_B$-I) 147° C.;

trans-2-(4-trifluoromethyl-phenyl)-5-[2-(trans-5-butyl-1,3-dioxan-2yl)-ethyl]-1,3-dioxane, m.p. (C-$S_B$) 118.5° C., cl.p. ($S_B$-I) 146° C.;

trans-2-(4-trifluoromethyl-phenyl)-5-[2-(trans-5-pentyl-1,3-dioxan-2yl)-ethyl]-1,3-dioxane;

(E)-trans-2-(4-trifluoromethyl-phenyl)-5-[2-(trans-5-propenyl-1,3-dioxan-2-yl)-ethyl]-1,3-dioxane, m.p. (C-$S_B$)148° C., cl.p. ($S_B$-I) 156.5° C.;

(E)-trans-2-(4-trifluoromethyl-phenyl)-5-[2-(trans-5-but-1-enyl-1,3-dioxan-2-yl)-ethyl]-1,3-dioxane, m.p. (C-$S_B$)150° C., cl.p. ($S_B$-I) 161° C.;

(E)-trans-2-(4-trifluoromethyl-phenyl)-5-[2-(trans-5-pent-1-enyl-1,3-dioxan-2-yl)-ethyl]-1,3-dioxane;

trans-2-(4-difluoromethoxy-phenyl)-5-[2-(trans-5-propyl-1,3-dioxan-2-yl)-ethyl]-1,3-dioxane;

trans-2-(4-difluoromethoxy-phenyl)-5-[2-(trans-5-butyl-1,3-dioxan-2-yl)-ethyl]-1,3-dioxane;

trans-2-(4-difluoromethoxy-phenyl)-5-[2-(trans-5-pentyl-1,3-dioxan-2-yl)-ethyl]-1,3-dioxane;

(E)-trans-2-(4-difluoromethoxy-phenyl)-5-[2-(trans-5-propenyl-1,3-dioxan -2-yl)-ethyl]-1,3-dioxane;

trans-2-(4-trifluoromethoxy-phenyl)-5-[2-(trans-5-propyl-1,3-dioxan-2-yl)-ethyl]-1,3-dioxane;

trans-2-(4-trifluoromethoxy-phenyl)-5-[2-(trans-5-butyl-1,3-dioxan-2-yl)-ethyl]-1,3-dioxane;

trans-2-(4-trifluoromethoxy-phenyl)-5-[2-(trans-5-pentyl-1,3-dioxan-2-yl)-ethyl]-1,3-dioxane;

(E)-trans-2-(4-trifluoromethoxy-phenyl)-5-[2-(trans-5-propenyl-1,3-dioxan-2-yl)-ethyl]-1,3-dioxane;

(E)-trans-2-(4-trifluoromethoxy-phenyl)-5-[2-(trans-5-but-1-enyl-1,3-dioxan-2-yl)-ethyl]-1,3-dioxane;

(E)-trans-2-(4-trifluoromethoxy-phenyl)-5-[2-(trans-5-pent-1-enyl-1,3-dioxan-2-yl)-ethyl]-1,3-dioxane;

trans-2-(4-trifluoromethoxy-phenyl)-5-[2-(trans-5-but-3-enyl-1,3-dioxan-2-yl)-ethyl]-1,3-dioxane;

trans-2-(4-trifluoromethoxy-phenyl)-5-[2-(trans-5-pent-4-enyl-1,3-dioxan-2-yl)-ethyl]-1,3-dioxane;

trans-2-(4-trifluoromethoxy-phenyl)-5-[2-[trans-5-(3-methoxypropyl)-1,3-dioxan-2-yl]-ethyl]-1,3-dioxane;

trans-2-[4-(2,2,2-trifluoroethoxy)-phenyl]-5-[2-(trans-5-propyl-1,3-dioxan-2-yl)-ethyl]-1,3-dioxane;

trans-2-[4-(2,2,2-trifluoroethoxy)-phenyl]-5-[2-(trans-5-butyl-1,3-dioxan-2-yl)-ethyl]-1,3-dioxane;

trans-2-[4-(2,2,2-trifluoroethoxy)-phenyl]-5-[2-(trans-5-pentyl-1,3-dioxan-2-yl)-ethyl]-1,3-dioxane;

(E)-trans-2-[4-(2,2,2-trifluoroethoxy)-phenyl]-5-[2-(trans-5-propenyl-1,3-dioxan-2-yl)-ethyl]-1,3-dioxane;

(E)-trans-2-[4-(2,2,2-trifluoroethoxy)-phenyl]-5-[2-(trans-5-but-1-enyl-1,3-dioxan-2-yl)-ethyl]-1,3-dioxane;

trans-2-(4-tolyl)-5-[2-(trans-5-propyl-1,3-dioxan-2-yl)-ethyl]-1,3-dioxane;

trans-2-(4-tolyl)-5-[2-(trans-5-pentyl-1,3-dioxan-2-yl)-ethyl]-1,3-dioxane;

trans-(4-propyl-phenyl)-5-[2-(trans-5-propyl-1,3-dioxan-2yl-ethyl]-1,3-dioxane;

trans-(4-propyl-phenyl)-5-[2-(trans-5-pentyl-1,3-dioxan-2yl)-ethyl]-1,3-dioxane;

trans-(4-ethoxy-phenyl)-5-[2-(trans-5-propyl-1,3-dioxan-2yl)-ethyl]-1,3-dioxane;

trans-2-(4-ethoxy-phenyl)-5-[2-(trans-5-pentyl-1,3-dioxan-2-yl)-ethyl]-1,3-dioxane;

trans-2-(3,4-difluoro-phenyl)-5-[2-(trans-5-propyl-1,3-dioxane-2-yl)-ethyl]-1,3-dioxan, m.p. (C-I) 82.9° C., S$_B$-N 76.4° C., cl.p. (N-I) 76.5° C.;

trans-2-(3,4-difluoro-phenyl)-5-[2-(trans-5-butyl-1,3-dioxane-2-yl)-ethyl]-1,3-dioxan, m.p. (C-I) 87.5° C., cl.p. (S$_B$-I) 78.7° C.;

trans-2-(3,4-difluoro-phenyl)-5-[2-(trans-5-pentyl-1,3-dioxan-2-yl)-ethyl]-1,3-dioxane;

trans-2-(3,4-difluoro-phenyl)-5-[2-(trans-5-hexyl-1,3-dioxan-2-yl)-ethyl]-1,3-dioxane;

(E)-trans-2-(3,4-difluoro-phenyl)-5-[2-(trans-5-propenyl-1,3-dioxan-2-yl)-ethyl]-1,3-dioxane, m.p. (C-I) 106.1° C., S$_B$-N 86.4° C., cl.p. (N-I) 97.3° C.;

(E)-trans-2-(3,4-difluoro-phenyl)-5-[2-(trans-5-but-1-enyl-1,3-dioxan-2-yl)-ethyl]-1,3-dioxane;

(E)-trans-2-(3,4-difluoro-phenyl)-5-[2-(trans-5-pent-1-enyl-1,3-dioxan-2-yl)-ethyl]-1,3-dioxane;

trans-2-(3,4-difluoro-phenyl)-5-[2-(trans-5-but-3-enyl-1,3-dioxan-2-yl)-ethyl]-1,3-dioxane;

trans-2-(3,4-difluoro-phenyl)-5-[2-[trans-5-(3-methoxy-propyl)-1,3-dioxan-2-yl]-ethyl]-1,3-dioxane;

trans-2-(4-chloro-3-fluoro-phenyl)-5-[2-(trans-5-propyl-1,3-dioxan-2-yl)-ethyl]-1,3-dioxane;

trans-2-(4-chloro-3-fluoro-phenyl)-5-[2-(trans-5-pentyl-1,3-dioxan-2-yl)-ethyl]-1,3-dioxane;

(E)-trans-2-(4-chloro-3-fluoro-phenyl)-5-[2-(trans-5-propenyl-1,3-dioxan-2-yl)-ethyl]-1,3-dioxane;

trans-2-(4-difluoromethoxy-3-fluoro-phenyl)-5-[2-(trans-5-propyl-1,3-dioxan-2-yl)-ethyl]-1,3-dioxane;

trans-2-(4-difluoromethoxy-3-fluoro-phenyl)-5-[2-(trans-5-butyl-1,3-dioxan-2-yl)-ethyl]-1,3-dioxane;

trans-2-(4-difluoromethoxy-3-fluoro-phenyl)-5-[2-(trans-5-pentyl-1,3-dioxan-2-yl)-ethyl]-1,3-dioxane;

(E)-trans-2-(4-difluoromethoxy-3-fluoro-phenyl)-5-[2-(trans-5-propenyl-1,3-dioxan-2-yl)-ethyl]-1,3-dioxane;

(E)-trans-2-(4-difluoromethoxy-3-fluoro-phenyl)-5-[2-(trans-5-pent-1-enyl-1,3-dioxan-2-yl)-ethyl]-1,3-dioxane;

trans-2-(3-fluoro-4-trifluoromethoxy-phenyl)-5-[2-(trans-5-propyl-1,3-dioxan-2-yl)-ethyl]-1,3-dioxane;

trans-2-(3-fluoro-4-trifluoromethoxy-phenyl)-5-[2-(trans-5-butyl-1,3-dioxan-2-yl)-ethyl]-1,3-dioxane;

trans-2-(3-fluoro-4-trifluoromethoxy-phenyl)-5-[2-(trans-5-pentyl-1,3-dioxan-2-yl)-ethyl]-1,3-dioxane;

(E)-trans-2-(3-fluoro-4-trifluoromethoxy-phenyl)-5-[2-(trans-5-propenyl-1,3-dioxan-2-yl)-ethyl]-1,3-dioxane;

(E)-trans-2-(3-fluoro-4-trifluoromethoxy-phenyl)-5-[2-(trans-5-but-1-enyl-1,3-dioxan-2-yl)-ethyl]-1,3-dioxane;

(E)-trans-2-(3-fluoro-4-trifluoromethoxy-phenyl)-5-[2-(trans-5-pent-1-enyl-1,3-dioxan-2-yl)-ethyl]-1,3-dioxane;

trans-2-[3-fluoro-4-(2,2,2-trifluoroethoxy-phenyl)-5-[2-(trans-5-propyl-1,3-dioxan-2-yl)-ethyl]-1,3-dioxane;

trans-2-[3-fluoro-4-(2,2,2-trifluoroethoxy-phenyl)-5-[2-(trans-5-butyl-1,3-dioxan-2-yl)-ethyl]-1,3-dioxane;

trans-2-[3-fluoro-4-(2,2,2-trifluoroethoxy-phenyl)-5-[2-(trans-5-pentyl-1,3-dioxan-2-yl)-ethyl]-1,3-dioxane;

trans-2-(3,4,5-trifluoro-phenyl)-5-[2-(trans-5-propyl-1,3-dioxan-2-yl)-ethyl]-1,3-dioxane, m.p. (C-I) 88.5° C.;

trans-2-(3,4,5-trifluoro-phenyl)-5-[2-(trans-5-butyl-1,3-dioxan-2-yl)-ethyl]-1,3-dioxane ;

trans-2-(3,4,5-trifluoro-phenyl)-5-[2-(trans-5-pentyl-1,3-dioxan-2-yl)-ethyl]-1,3-dioxane;

trans-2-(3,4,5-trifluoro-phenyl)-5-[2-(trans-5-hexyl-1,3-dioxan-2-yl)-ethyl]-1,3-dioxane;

(E)-trans-2-(3,4,5-trifluoro-phenyl)-5-[2-(trans-5-propenyl-1,3-dioxan-2-yl)-ethyl]-1,3-dioxane, m.p. (C-I) 112.7° C., cl.p. (N-I) 63.6° C.;

(E)-trans-2-(3,4,5-trifluoro-phenyl)-5-[2-(trans-5-but-1-enyl-1,3-dioxan-2-yl)-ethyl]-1,3-dioxane;

(E)-trans-2-(3,4,5-trifluoro-phenyl)-5-[2-(trans-5-pent-1-enyl-1,3-dioxan-2-yl)-ethyl]-1,3-dioxane;

trans-2-(3,4,5-trifluoro-phenyl)-5-[2-(trans-5-but-3-enyl-1,3-dioxan-2-yl)-ethyl]-1,3-dioxane;

trans-2-(3,4,5-trifluoro-phenyl)-5-[2-(trans-5-pent-4-enyl-1,3-dioxan-2-yl)-ethyl]-1,3-dioxane;

trans-2-(4-difluoromethoxy-3,5-difluoro-phenyl)-5-[2-(trans-5-propyl-1,3-dioxan-2-yl)-ethyl]-1,3-dioxane;

trans-2-(4-difluoromethoxy-3,5-difluoro-phenyl)-5-[2-(trans-5-butyl-1,3-dioxan-2-yl)-ethyl]-1,3-dioxane;

trans-2-(4-difluoromethoxy-3,5-difluoro-phenyl)-5-[2-(trans-5-pentyl-1,3-dioxan-2-yl)-ethyl]-1,3-dioxane;

(E)-trans-2-(4-difluoromethoxy-3,5-difluoro-phenyl)-5-[2-(trans-5-propenyl-1,3-dioxan-2-yl)-ethyl]-1,3-dioxane;

(E)-trans-2-(4-difluoromethoxy-3,5-difluoro-phenyl)-5-[2-(trans-5-but-1-enyl-1,3-dioxan-2-yl)-ethyl]-1,3-dioxane;

(E)-trans-2-(4-difluoromethoxy-3,5-difluoro-phenyl)-5-[2-(trans-5-pent-1-enyl-1,3-dioxan-2-yl)-ethyl]-1,3-dioxane;

trans-2-[3,5-difluoro-4-(2,2,2-trifluoroethoxy)-phenyl]-5-[2-(trans-5-propyl-1,3-dioxan-2-yl)-ethyl]-1,3-dioxane;

trans-2-[3,5-difluoro-4-(2,2,2-trifluoroethoxy)-phenyl]-5-[2-(trans-5-butyl-1,3-dioxan-2-yl)-ethyl]-1,3-dioxane;

trans-2-[3,5-difluoro-4-(2,2,2-trifluoroethoxy)-phenyl]-5-[2-(trans-5-pentyl-1,3-dioxan-2-yl)-ethyl]-1,3-dioxane;

(E)-trans-2-[3,5-difluoro-4-(2,2,2-trifluoroethoxy)-phenyl]-5-[2-(trans-5-propenyl-1,3-dioxan-2-yl)-ethyl]-1,3-dioxane;

(E)-trans-2-[3,5-difluoro-4-(2,2,2-trifluoroethoxy)-phenyl]-5-[2-(trans-5-but-1-enyl-1,3-dioxan-2-yl)-ethyl]-1,3-dioxane;

(E)-trans-2-[3,5-difluoro-4-(2,2,2-trifluoroethoxy)-phenyl]-5-[2-(trans-5-pent-1-enyl-1,3-dioxan-2-yl)-ethyl]-1,3-dioxane;

4-[trans-5-[2-(trans-5-butyl-1,3-dioxan-2-yl)-ethyl]-1,3-dioxan-2-yl]-phenyl isothiocyanate;

4-[trans-5-[2-(trans-5-propyl-1,3-dioxan-2-yl)-ethyl]-1,3-dioxane-2-yl]-benzonitrile;

4-[trans-5-[2-(trans-5-butyl-1,3-dioxan-2-yl)-ethyl]-1,3-dioxan-2-yl]-benzonitrile;

4-[trans-5-[2-(trans-5-pentyl-1,3-dioxan-2-yl)-ethyl]-1,3-dioxan-2-yl]-benzonitrile;

(E)-4-[trans-5-[2-(trans-5-propenyl-1,3-dioxan-2-yl)-ethyl]-1,3-dioxan-2-yl]-benzonitrile;

(E)-4-[trans-5-[2-(trans-5-but-1-enyl-1,3-dioxan-2-yl)-ethyl]-1,3-dioxan-2-yl]-benzonitrile;

trans-2-(2,3-difluoro-4-propyl-phenyl)-5-[2-(trans-5-butyl-1,3-dioxan-2-yl)-ethyl]-1,3-dioxane;

trans-2-(2,3-difluoro-4-pentyl-phenyl)-5-[2-(trans-5-butyl-1,3-dioxan-2-yl)-ethyl]-1,3-dioxane;

trans-2-(2,3-difluoro-4-ethoxy-phenyl)-5-[2-(trans-5-butyl-1,3-dioxan-2-yl)-ethyl]-1,3-dioxane;

trans-2-(2,3-difluoro-4-butoxy-phenyl)-5-[2-(trans-5-butyl-1,3-dioxan-2-yl)-ethyl]-1,3-dioxane;

trans-2-(6-butyl-2-naphthyl)-5-[2-(trans-5-butyl-1,3-dioxan-2-yl)-ethyl]-1,3-dioxane;

trans-2-(6-ethoxy-2-naphthyl)-5-[2-(trans-5-butyl-1,3-dioxan-2-yl)-ethyl]-1,3-dioxane;

trans-2-(6-butoxy-2-naphthyl)-5-[2-(trans-5-butyl-1,3-dioxan-2-yl)-ethyl]-1,3-dioxane;

trans-2-(2-pentyl-5-pyridyl)-5-[2-(trans-5-butyl-1,3-dioxan-2-yl)-ethyl]-1,3-dioxane;

trans-2-(2-butyl-5-pyrimidyl)-5-[2-(trans-5-butyl-1,3-dioxan-2-yl)-ethyl]-1,3-dioxane;

trans-2-(4-fluoro-3-cyclohexenyl)-5-[2-(trans-5-propyl-1,3-dioxan-2-yl)-ethyl]-1,3-dioxane;

trans-2-(4-fluoro-3-cyclohexenyl)-5-[2-(trans-5-butyl-1,3-dioxan-2-yl)-ethyl]-1,3-dioxane;

trans-2-(4-fluoro-3-cyclohexenyl)-5-[2-(trans-5-pentyl-1,3-dioxan-2-yl)-ethyl]-1,3-dioxane;

(E)-trans-2-(4-fluoro-3-cyclohexenyl)-5-[2-(trans-5-propenyl-1,3-dioxan-2-yl)-ethyl]-1,3-dioxane;

(E)-trans-2-(4-fluoro-3-cyclohexenyl)-5-[2-(trans-5-but-1-enyl-1,3-dioxan-2-yl)-ethyl]-1,3-dioxane;

trans-2-(4-trifluoromethyl-3-cyclohexenyl)-5-[2-(trans-5-butyl-1,3-dioxan-2-yl)-ethyl]-1,3-dioxane.

EXAMPLE 2

A solution of 1.72 g of (E)-2-[4-(5-but-1-enyl-1,3-dioxan-2-yl)butyl]-1,3-propanediol and 1.0 g of 3,4-difluorobenzaldehyde in 30 ml of benzene is heated to slight boiling with 35 mg of p-toluenesulfonic acid monohydrate for 1 hour. After neutralization of the solution with a few drops of triethylamine the mixture is washed with water, dried over sodium sulfate, filtered and the filtrate is evaporated. The crude product is chromatographed on 40 g of silica gel with hexane/ethyl acetate 5% (v/v). Two-fold crystallization of the resulting isomer mixture from hexane yields pure (E)-trans-2-(3,4-difluorophenyl)-5-[4-(trans-5-but-1-enyl-1,3-dioxane.

The (E)-2-[4-(5-but-1-enyl-1,3-dioxan-2-yl)-butyl]-1,3-propanediol used as the starting material is prepared starting from 2-(4-bromobutyl)-dioxolane in an analogous manner to the ethyl derivative described in Example 1.

The following compounds can be prepared in an analogous manner:

trans-2-(3,4-difluoro-phenyl)-5-[4-(trans-5-butyl-1,3-dioxan-2-yl)-butyl]-1,3-dioxane;

trans-2-(3,4,5-trifluoro-phenyl)-5-[4-(trans-5-butyl-1,3-dioxan-2-yl)-butyl]-1,3-dioxane;

trans-2-(4-trifluoromethoxy-phenyl)-5-[4-(trans-5-butyl-1,3-dioxan-2-yl)-butyl]-1,3-dioxane;

trans-2-(4-difluoromethoxy-3-fluoro-phenyl)-5-[4-(trans-5-butyl-1,3-dioxan-2-yl)-butyl]-1,3-dioxane;

trans-2-(4-difluoromethoxy-3,5-difluoro-phenyl)-5-[4-(trans-5-butyl-1,3-dioxan-2-yl)-butyl]-1,3-dioxane;

trans-2-[4-(2,2,2-trifluoroethoxy)-phenyl]-5-[4-(trans-5-butyl-1,3-dioxan-2-yl)-butyl]-1,3-dioxane;

trans-2-[3-fluoro-4-(2,2,2-trifluoroethoxy)-phenyl]-5-[4-(trans-5-butyl-1,3-dioxan-2-yl)-butyl]-1,3-dioxane;

trans-2-[3,5-difluoro-4-(2,2,2-trifluoroethoxy)-phenyl]-5-[4-(trans-5-butyl-1,3-dioxan-2-yl)-butyl]-1,3-dioxane;

trans-2-(4-chloro-3-fluoro-phenyl)-5-[4-(trans-5-butyl-1,3-dioxan-2-yl)-butyl]-1,3-dioxane;

trans-2-(4-cyanophenyl)-5-[4-(trans-5-butyl-1,3-dioxan-2-yl)-butyl]-1,3-dioxane;

trans-2-(trans-4-pentylcyclohexyl)-5-[4-(trans-5-butyl-1,3-dioxan-2-yl)-butyl]-1,3-dioxane;

trans-2-pentyl-5-[4-(trans-5-butyl-1,3-dioxan-2-yl)-butyl]-1,3-dioxane;

trans-2-butyl-5-[4-(trans-5-butyl-1,3-dioxan-2-yl)-butyl]-1,3-dioxane.

EXAMPLE 3

A solution of 1.2 g of 2-(5-butyl-1,3-dioxan-2-yl)-1,3-propanediol and 2.4 ml of caproaldehyde was treated with 14 mg of p-toluenesulfonic acid monohydrate and stirred at 70° C. for 45 minutes. The reaction mixture was neutralized with a few drops of triethylamine and, after cooling, washed with saturated sodium chloride solution, dried over sodium sulphate, filtered and the filtrate was concentrated. The crude product (1.92 g) was chromatographed on 50 g of silica gel with hexane/ethyl acetate 5% (v/v). 1.52 g of isomer mixture with a 44% trans/trans content (GC) were obtained. Two-fold recrystallization from hexane gave 0.42 g of pure trans-5-butyl-trans-2'-pentyl-2,5'-bi-1,3-dioxane, m.p. (C-$S_B$) 93.3° C., cl.p. ($S_B$-I) 127.0° C.

The 2-(5-butyl-1,3-dioxan-2-yl)-1,3-propanediol used as the starting material was prepared as follows:

a) A mixture of 17.45 g of 2-butyl-1,3-propanediol, 26.4 g of diethyl (ethoxymethylidene)-malonate, 250 ml of toluene and 0.285 g of p-toluenesulfonic acid monohydrate was heated to boiling for 1 hour, with moist toluene being distilled off and replaced by the addition of fresh toluene. The reaction mixture was neutralized with triethylamine and, after cooling, washed with saturated sodium chloride solution, dried over sodium sulphate and concentrated. The crude product (42.35 g) was chromatographed on 520 g of silica gel with hexane/ethyl acetate (4:1). 33.0 g of oily diethyl (5-butyl-1,3-dioxan-2-yl)-malonate were obtained.

b) A solution of 33.0 g of diethyl (5-butyl-1,3-dioxan-2-yl)-malonate in 200 ml of tetrahydrofuran was added dropwise within 2 hours at 3°–5° C. to a suspension of 8.35 g of lithium aluminium hydride in 300 ml of tetrahydrofuran. The reaction mixture was stirred at 5° C. for a further 15 minutes and at room temperature for 2 hours. After cooling 3N sodium hydroxide solution was cautiously added dropwise until a white clump settled out. The solution was decanted and the residue was washed several times with diethyl ether. The combined organic phases were washed with 40 ml of concentrated sodium bicarbonate solution and five times with 40 ml of concentrated sodium chloride solution each time., dried over sodium sulfate, filtered and concentrated. The crude product (22.8 g) was used in the next step without further purification; according to GC it contained 93% of 2-(5-butyl-1,3-dioxan-2-yl)-1,3-propanediol (trans/cis ratio 2.3:1).

In an analogous manner there can be prepared:

trans,trans-5,2'-dipropyl-2,5'-bi-1,3-dioxane, m.p. (C-$S_B$) 85.4° C., cl.p. ($S_B$-I) 125.5° C.

trans-5-propyl-trans-2'-butyl-2,5'-bi-1,3-dioxane;

trans-5-propyl-trans-2'-pentyl-2,5'-bi-1,3-dioxane;

trans-5-butyl-trans-2'-propyl-2,5'-bi-1,3-dioxane;

trans,trans-5,2'-dibutyl-2,5'-bi-1,3-dioxane;

trans-5-pentyl-trans-2'-propyl-2,5'-bi-1,3-dioxane;

trans-5-pentyl-trans-2'-butyl-2,5'-bi-1,3-dioxane;

trans,trans-5,2'-dipentyl-2,5'-bi-1,3-dioxane, m.p. (C-S$_B$) 92.8° C., cl.p. (S$_B$-I) 134.0° C.

(E)-trans-5-propenyl-trans-2'-propyl-2,5'-bi-1,3-dioxane;

(E)-trans-5-propenyl-trans-2'-butyl-2,5'-bi-1,3-dioxane;

(E)-trans-5-propenyl-trans-2'-pentyl-2,5'-bi-1,3-dioxane;

(E)-trans-5-but-1-enyl-trans-2'-propyl-2,5'-bi-1,3-dioxane;

(E)-trans-5-but-1-enyl-trans-2'-butyl-2,5'-bi-1,3-dioxane;

(E)-trans-5-but-1-enyl-trans-2'-pentyl-2,5'-bi-1,3-dioxane;

(E)-trans-5-pent-1-enyl-trans-2-propyl-2,5'-bi-1,3-dioxane;

(E)-trans-5-pent-1-enyl-trans-2-butyl-2,5'-bi-1,3-dioxane;

(E)-trans-5-pent-1-enyl-trans-2-pentyl-2,5'-bi-1,3-dioxane;

(E)-trans-5-but-3-enyl-trans-2-butyl-2,5'-bi-1,3-dioxane;

trans-5-propyl-trans-2'-(trans-4-propylcyclohexyl)-2,5'-bi-1,3-dioxane;

trans-5-propyl-trans-2'-(trans-4-butylcyclohexyl)-2,5'-bi-1,3-dioxane;

trans-5-propyl-trans-2'-(trans-4-pentylcyclohexyl)-2,5'-bi-1,3-dioxane;

trans-5-butyl-trans-2'-(trans-4-propylcyclohexyl)-2,5'-bi-1,3-dioxane;

trans-5-butyl-trans-2'-(trans-4-butylcyclohexyl)-2,5'-bi-1,3-dioxane;

trans-5-butyl-trans-2'-(trans-4-pentylcyclohexyl)-2,5'-bi-1,3-dioxane;

trans-5-pentyl-trans-2'-(trans-4-propylcyclohexyl)-2,5'-bi-1,3-dioxane;

trans-5-pentyl-trans-2'-(trans-4-butylcyclohexyl)-2,5'-bi-1,3-dioxane;

trans-5-pentyl-trans-2'-(trans-4-pentylcyclohexyl)-2,5'-bi-1,3-dioxane;

(E)-trans-5-but-1-enyl-trans-2'-(trans-4-butylcyclohexyl)-2,5'-bi-1,3-dioxane;

trans-5-propyl-trans-2'-(4-fluorophenyl)-2,5'-bi-1,3-dioxane;

trans-5-butyl-trans-2'-(4-fluorophenyl)-2,5'-bi-1,3-dioxane;

trans-5-pentyl-trans-2'-(4-fluorophenyl)-2,5'-bi-1,3-dioxane;

(E)-trans-5-propenyl-trans-2'-(4-fluorophenyl)-2,5'-bi-1,3-dioxane;

(E)-trans-5-but-1-enyl-trans-2'-(4-fluorophenyl)-2,5'-bi-1,3-dioxane;

trans-5-butyl-trans-2'-(4-chlorophenyl)-2,5'-bi-1,3-dioxane;

trans-5-pentyl-trans-2'-(4-chlorophenyl)-2,5'-bi-1,3-dioxane;

trans-5-propyl-trans-2'-(4-trifluoromethyl-phenyl)-2,5'-bi-1,3-dioxane, m.p. (C-S$_B$) 143.4° C., cl.p. (S$_B$-I) 188.5° C.;

trans-5-butyl-trans-2'-(4-trifluoromethyl-phenyl)-2,5'-bi-1,3-dioxane, m.p. (C-S$_B$) 115.0° C., cl.p. (S$_B$-I) 174.5° C.;

trans-5-pentyl-trans-2'-(4-trifluoromethyl-phenyl)-2,5'-bi-1,3-dioxane, m.p. (C-S$_B$) 101.1° C., cl.p. (S$_B$-I) 184.0° C.;

(E)-trans-5-propenyl-trans-2'-(4-trifluoromethyl-phenyl)-2,5'-bi-1,3-dioxane;

(E)-trans-5-but-1-enyl-trans-2'-(4-trifluoromethyl-phenyl)-2,5'-bi-1,3-dioxane;

(E)-trans-5-pent-1-enyl-trans-2'-(4-trifluoromethyl-phenyl)-2,5'-bi-1,3-dioxane;

trans-5-propyl-trans-2'-(4-trifluoromethoxy-phenyl)-2,5'-bi-1,3-dioxane, m.p. (C-S$_B$) 125.2° C., cl.p. (S$_B$-I) 195.8° C.;

trans-5-butyl-trans-2'-(4-trifluoromethoxy-phenyl)-2,5'-bi-1,3-dioxane, m.p. (C-S$_B$) 102.7° C., cl.p. (S$_B$-I) 194.3° C.;

trans-5-pentyl-trans-2'-(4-trifluoromethoxy-phenyl)-2,5'-bi-1,3-dioxane, m.p. (C-S$_B$) 108° C., cl.p. (S$_B$-I) 192° C.;

(E)-trans-5-but-1-enyl-trans-2'-(4-trifluoromethoxy-phenyl)-2,5'-bi-1,3-dioxane;

trans-5-propyl-trans-2'-(4-difluoromethoxy-phenyl)-2,5'-bi-1,3-dioxane;

trans-5-butyl-trans-2'-(4-difluoromethoxy-phenyl)-2,5'-bi-1,3-dioxane;

trans-5-pentyl-trans-2'-(4-difluoromethoxy-phenyl)-2,5'-bi-1,3-dioxane;

trans-5-butyl-trans-2'-[4-(2,2,2-trifluoroethoxy)-phenyl]-2,5'-bi-1,3-dioxane;

trans-5-pentyl-trans-2'-[4-(2,2,2-trifluoroethoxy)-phenyl]-2,5'-bi-1,3-dioxane;

trans-5-butyl-trans-2'-(4-tolyl)-2,5'-bi-1,3-dioxane;

trans-5-pentyl-trans-2'-(4-tolyl)-2,5'-bi-1,3-dioxane;

trans-5-propyl-trans-2'-(4-propylphenyl)-2,5'-bi-1,3-dioxane;

trans-5-butyl-trans-2'-(4-propylphenyl)-2,5'-bi-1,3-dioxane;

trans-5-pentyl-trans-2'-(4-propylphenyl)-2,5'-bi-1,3-dioxane;

trans-5-propyl-trans-2'-(4-ethoxy-phenyl)-2,5'-bi-1,3-dioxane;

trans-5-pentyl-trans-2'-(4-ethoxy-phenyl)-2,5'-bi-1,3-dioxane;

trans-5-propyl-trans-2'-(3,4-difluoro-phenyl)-2,5'-bi-1,3-dioxane, m.p. (C-S$_B$) 127.7° C., cl.p. (S$_B$-I) 139.5° C.;

trans-5-butyl-trans-2'-(3,4-difluoro-phenyl)-2,5'-bi-1,3-dioxane, m.p. (C-S$_B$) 102.0° C., cl.p. (S$_B$-I) 132.1° C.;

trans-5-pentyl-trans-2'-(3,4-difluoro-phenyl)-2,5'-bi-1,3-dioxane, m.p. (C-S$_B$) 95.5° C., S$_B$-S$_2$ 116.5, S$_2$-S$_A$ 121.8, cl.p. (S$_A$-I) 124.8° C.;

(E)-trans-5-propenyl-trans-2'-(3,4-difluoro-phenyl)-2,5'-bi-1,3-dioxane;

(E)-trans-5-but-1-enyl-trans-2'-(3,4-difluoro-phenyl)-2,5'-bi-1,3-dioxane;

(E)-trans-5-pent-1-enyl-trans-2'-(3,4-difluoro-phenyl)-2,5'-bi-1,3-dioxane;

trans-5-but-3-enyl-trans-2'-(3,4-difluoro-phenyl)-2,5'-bi-1,3-dioxane;

trans-5-pent-4-enyl-trans-2'-(3,4-difluoro-phenyl)-2,5'-bi-1,3-dioxane;

trans-5-propyl-trans-2'-(4-chloro-3-fluoro-phenyl)-2,5'-bi-1,3-dioxane;

trans-5-butyl-trans-2'-(4-chloro-3-fluoro-phenyl)-2,5'-bi-1,3-dioxane;

trans-5-pentyl-trans-2'-(4-chloro-3-fluoro-phenyl)-2,5'-bi-1,3-dioxane;

trans-5-propyl-trans-2'-(4-difluoromethoxy-3-fluoro-phenyl)-2,5'-bi-1,3-dioxane;

trans-5-butyl-trans-2'-(4-difluoromethoxy-3-fluoro-phenyl)-2,5'-bi-1,3-dioxane;

trans-5-pentyl-trans-2'-(4-difluoromethoxy-3-fluoro-phenyl-2,5'-bi-1,3-dioxane;

(E)-trans-5-propenyl-trans-2'-(4-difluoromethoxy-3-fluoro-phenyl)-2,5'-bi-1,3-dioxane;

(E)-trans-5-but-1-enyl-trans-2'-(4-difluoromethoxy-3-fluoro-phenyl)-2,5'-bi-1,3-dioxane;

(E)-trans-5-pent-1-enyl-trans-2'-(4-difluoromethoxy-3-fluoro-phenyl)-2,5'-bi-1,3-dioxane;

trans-5-propyl-trans-2'-(3-fluoro-4-trifluoromethoxy-phenyl)-2,5'-bi-1,3-dioxane;

trans-5-butyl-trans-2'-(3-fluoro-4-trifluoromethoxy-phenyl)-2,5'-bi-1,3-dioxane;

trans-5-pentyl-trans-2'-(3-fluoro-4-trifluoromethoxy-phenyl)-2,5-bi-1,3-dioxane;

trans-5-propyl-trans-2-[3-fluoro-4-(2,2,2-trifluoroethoxy)-phenyl]-2,5'-bi-1,3-dioxane;

trans-5-butyl-trans-2-[3-fluoro-4-(2,2,2-trifluoroethoxy)-phenyl]-2,5'-bi-1,3-dioxane;

trans-5-pentyl-trans-2-[3-fluoro-4-(2,2,2-trifluoroethoxy)-phenyl]-2,5'-bi-1,3-dioxane;

trans-5-propyl-trans-2'-(3,4,5-trifluoro-phenyl)-2,5'-bi-1,3-dioxane, m.p. (C-I) 117.3° C.;

trans-5-butyl-trans-2'-(3,4,5-trifluoro-phenyl)-2,5'-bi-1,3-dioxane, m.p. (C-I) 99.8° C., cl.p. ($S_A$-I) 91.5° C.;

trans-5-pentyl-trans-2'-(3,4,5-trifluoro-phenyl)-2,5'-bi-1,3-dioxane, m.p. (C-I) 93.8° C., cl.p. ($S_A$-I) 92.0° C.;

(E)-trans-5-propenyl-trans-2'-(3,4,5-trifluoro-phenyl)-2,5'-bi-1,3-dioxane;

(E)-trans-5-but-1-enyl-trans-2'-(3,4,5-trifluoro-phenyl)-2,5'-bi-1,3-dioxane;

trans-5-propyl-trans-2'-(4-difluoromethoxy-3,5-difluoro-phenyl)-2,5'-bi-1,3-dioxane;

trans-5-butyl-trans-2'-(4-difluoromethoxy-3,5-difluoro-phenyl)-2,5'-bi-1,3-dioxane;

trans-5-pentyl-trans-2'-(4-difluoromethoxy-3,5-difluoro-phenyl)-2,5'-bi-1,3-dioxane;

(E)-trans-5-propenyl-trans-2'-(4-difluoromethoxy-3,5-difluoro-phenyl)-2,5'-bi-1,3-dioxane;

(E)-trans-5-but-1-enyl-trans-2'-(4-difluoromethoxy-3,5-difluoro-phenyl)-2,5'-bi-1,3-dioxane;

trans-5-propyl-trans-2'-[3,5-difluoro-4-(2,2,2-trifluoroethoxy)-phenyl]- 2,5'-bi-1,3-dioxane;

trans-5-butyl-trans-2'-[3,5-difluoro-4-(2,2,2-trifluoroethoxy)-phenyl]-2,5'-bi-1,3-dioxane;

trans-5-pentyl-trans-2'-[3,5-difluoro-4-(2,2,2-trifluoroethoxy)-phenyl]-2,5'-bi-1,3-dioxane;

(E)-trans-5-propenyl-trans-2'-[3,5-difluoro-4-(2,2,2-trifluoroethoxy)-phenyl]-2,5'-bi-1,3-dioxane;

(E)-trans-5-but-1-enyl-trans-2'-[3,5-difluoro-4-(2,2,2-trifluoroethoxy)-phenyl]-2,5'-bi-1,3-dioxane;

4-(trans-5-propyl-[2,5'-bi-1,3-dioxan]-trans-2'-yl)-benzonitrile;

4-(trans-5-butyl-[2,5'-bi-1,3-dioxan]-trans-2'-yl)-benzonitrile;

4-(trans-5-pentyl-[2,5'-bi-1,3-dioxan]-trans-2'-yl)-benzonitrile;

4-(trans-5-propyl-[2,5'-bi-1,3-dioxan]-trans-2'-yl)-2-fluoro-benzonitrile;

4-(trans-5-butyl-[2,5'-bi-1,3-dioxan]-trans-2'-yl)-2-fluoro-benzonitrile;

4-(trans-5-pentyl-[2,5'-bi-1,3-dioxan]-trans-2'-yl)-2-fluoro-benzonitrile;

trans-5-propyl-trans-2'-(4-fluoro-3-cyclohexenyl)-2,5'-bi-1,3-dioxane;

trans-5-butyl-trans-2'-(4-fluoro-3-cyclohexenyl)-2,5'-bi-1,3-dioxane, m.p. (C-$S_B$) 117.7° C., cl.p. ($S_B$-I) 137.5° C.;

trans-5-pentyl-trans-2'-(4-fluoro-3-cyclohexenyl)-2,5'-bi-1,3-dioxane;

(E)-trans-5-propenyl-trans-2'-(4-fluoro-3-cyclohexenyl)-2,5'-bi-1,3-dioxane;

(E)-trans-5-but-1-enyl-trans-2'-(4-fluoro-3-cyclohexenyl)-2,5'-bi-1,3-dioxane;

trans-5-propyl-trans-2'-(4-trifluoromethyl-3-cyclohexenyl)-2,5'-bi-1,3-dioxane;

trans-5-butyl-trans-2'-(4-trifluoromethyl-3-cyclo-5-hexenyl)-2,5'-bi-1,3-dioxane;

trans-5-pentyl-trans-2'-(4-trifluoromethyl-3-cyclohexenyl)-2,5'-bi-1,3-dioxane.

EXAMPLE 4

A mixture of 921 mg of 1,2-difluoro-4-(3-methoxyallyl)benzene, 1133 mg of 2-(5-butyl-1,3-dioxan-2-yl)-1,3-propanediol, 25 ml of benzene and 14.8 mg of p-toluenesulfonic acid monohydrate was heated to 74° C. for 1 hour, then neutralized with 5 drops of triethylamine and diluted with 40 ml of diethyl ether. The organic phase was separated, washed twice with 10 ml of water each time, dried over sodium sulfate, filtered and the filtrate was concentrated. The yellowish semi-solid crude product (1.82 g) was chromatographed on 23 g of silica gel with hexane/5% ethyl acetate. Two-fold recrystallization of the resulting isomer mixture (1294 mg) from hexane yielded 403 mg of pure trans-5-butyl-trans-2'-(3,4-difluoro-phenethyl)-2,5'-bi-1,3-dioxane, m.p. (C-$S_B$) 89.9° C., cl.p. ($S_B$-I) 110.4° C.

In an analogous manner there can be prepared:

trans-5-propyl-trans-2'-(4-fluoro-phenethyl)-2,5'-bi-1,3-dioxane;

trans-5-butyl-trans-2'-(4-fluoro-phenethyl)-2,5'-bi-1,3-dioxane;

trans-5-pentyl-trans-2'-(4-fluoro-phenethyl)-2,5'-bi-1,3-dioxane;

trans-5-butyl-trans-2'-(4-chloro-phenethyl)-2,5'-bi-1,3-dioxane;

trans-5-propyl-trans-2-(4-trifluoromethyl-phenethyl)-2,5'-bi-1,3-dioxane;

trans-5-butyl-trans-2'-(4-trifluoromethyl-phenethyl)-2,5'-bi-1,3-dioxane;

trans-5-pentyl-trans-2'-(4-trifluoromethyl-phenethyl)-2,5'-bi-1,3-dioxane;

trans-5-propyl-trans-2'-(4-trifluoromethoxy-phenethyl)-2,5'-bi-1,3-dioxane;

trans-5-butyl-trans-2'-(4-trifluoromethoxy-phenethyl)-2,5'-bi-1,3-dioxane, m.p. (C-$S_B$) 93.1° C., cl.p. ($S_B$-I) 158.3° C.;

trans-5-pentyl-trans-2'-(4-trifluoromethoxy-phenethyl)-2,5'-bi-1,3-dioxane;

(E)-trans-5-propenyl-trans-2'-(4-trifluoromethoxy-phenethyl)-2,5'-bi-1,3-dioxane;

(E)-trans-5-but-1-enyl-trans-2'-(4-trifluoromethoxy-phenethyl)-2,5'-bi-1,3-dioxane;

trans-5-propyl-trans-2'-(4-difluoromethoxy-phenethyl)-2,5'-bi-1,3-dioxane;

trans-5-butyl-trans-2'-(4-difluoromethoxy-phenethyl)-2,5'-bi-1,3-dioxane;

trans-5-pentyl-trans-2'-(4-difluoromethoxy-phenethyl)-2,5'-bi-1,3-dioxane;

trans-5-propyl-trans-2'-[4-(2,2,2-trifluoroethoxy)-phenethyl]-2,5'-bi-1,3-dioxane;

trans-5-propyl-trans-2'-(3,4-difluoro-phenethyl)-2,5'-bi-1,3-dioxane, m.p. (C-$S_B$) 100.3° C., cl.p. ($S_B$-I) 105.5° C.;

trans-5-pentyl-trans-2'-(3,4-difluoro-phenethyl)-2,5'-bi-1,3-dioxane, m.p. (C-$S_B$) 96.0° C., cl.p. ($S_B$-I) 112.0° C.;

trans-5-hexyl-trans-2'-(3,4-difluoro-phenethyl)-2,5'-bi-1,3-dioxane;

(E)-trans-5-propenyl-trans-2'-(3,4-difluoro-phenethyl)-2,5'-bi-1,3-dioxane;

(E)-trans-5-but-1-enyl-trans-2'-(3,4-difluoro-phenethyl)-2,5'-bi-1,3-dioxane;

(E)-trans-5-pent-1-enyl-trans-2'-(3,4-difluoro-phenethyl)-2,5'-bi-1,3-dioxane;

trans-5-but-3-enyl-trans-2'-(3,4-difluoro-phenethyl)-2,5'-bi-1,3-dioxane;

trans-5-pent-4-enyl-trans-2'-(3,4,-difluoro-phenyl-2,5'-bi-1,3-dioxane;

trans-5-(3-methoxy-propyl)-trans-2'-(3,4-difluoro-phenethyl)-2,5'-bi-1,3-dioxane;

trans-5-propyl-trans-2'-(4-chloro-3-fluoro-phenethyl)-2,5'-bi-1,3-dioxane;

trans-5-butyl-trans-2'-(4-chloro-3-fluoro-phenethyl)-2,5'-bi-1,3-dioxane;

trans-5-pentyl-trans-2'-(4-chloro-3-fluoro-phenethyl)-2,5'-bi-1,3-dioxane;

trans-5-propenyl-trans-2'-(4-chloro-3-fluoro-phenethyl)-2,5'-bi-1,3-dioxane;

trans-5-propyl-trans-2'-(3-fluoro-4-trifluoromethoxy-phenethyl)-2,5'-bi-1,3-dioxane;

trans-5-butyl-trans-2'-(3-fluoro-4-trifluoromethoxy-phenethyl)-2,5'-bi-1,3-dioxane;

trans-5-propyl-trans-2'-(4-difluoromethoxy-3-fluoro-phenethyl)-2,5'-bi-1,3-dioxane;

trans-5-butyl-trans-2'-(4-difluoromethoxy-3-fluoro-phenethyl)-2,5'-bi-1,3-dioxane;

trans-5-pentyl-trans-2'-(4-difluoromethoxy-3-fluoro-phenethyl)-2,5'-bi-1,3-dioxane;

(E)-trans-5-propenyl-trans-2'-(4-difluoromethoxy-3-fluoro-phenethyl)-2,5'-bi-1,3-dioxane;

(E)-trans-5-but-1-enyl-trans-2'-(4-difluoromethoxy-3-fluoro-phenethyl)-2,5'-bi-1,3-dioxane trans-5-butyl-trans-2'-[3-fluoro-4-(2,2,2-trifluoro-ethoxy)-phenethyl]-2,5'-bi-1,3-dioxane;

trans-5-butyl-trans-2'-(3-chloro-4-trifluoromethyl-phenethyl)-2,5'-bi-1,3-dioxane;

trans-5-propyl-trans-2'-(3,4,5-trifluoro-phenethyl)-2,5'-bi-1,3-dioxane;

trans-5-butyl-trans-2'-(3,4,5-trifluoro-phenethyl)-2,5'-bi-1,3-dioxane;

trans-5-pentyl-trans-2'-(3,4,5-trifluoro-phenethyl)-2,5'-bi-1,3-dioxane;

(E)-trans-5-propenyl-trans-2'-(3,4,5-trifluoro-phenethyl)-2,5'-bi-1,3-dioxane;

(E)-trans-5-but-1-enyl-trans-2'-(3,4,5-trifluoro-phenethyl)-2,5'-bi-1,3-dioxane;

trans-5-propyl-trans-2'-(4-difluoromethoxy-3,5-difluoro-phenethyl)-2,5'-bi-1,3-dioxane, m.p. (C-I) 91.6° C., cl.p. ($S_B$-I) 89.0° C.;

trans-5-butyl-trans-2'-(4-difluoromethoxy-3,5-difluoro-phenethyl)-2,5'-bi-1,3-dioxane, m.p. (C-$S_B$) 78.3° C., cl.p. ($S_B$-I) 95.7° C.;

trans-5-pentyl-trans-2'-(4-difluoromethoxy-3,5-difluoro-phenethyl)-2,5'-bi-1,3-dioxane;

(E)-trans-5-propenyl-trans-2'-(4-difluoromethoxy-3,5-difluoro-phenethyl)-2,5'-bi-1,3-dioxane;

(E)-trans-5-but-1-enyl-trans-2'-(4-difluoromethoxy-3,5-difluoro-phenethyl)-2,5'-bi-1,3-dioxane;

trans-5-butyl-trans-2'-[3,5-difluoro-4-(2,2,2-trifluoroethoxy)-phenethyl]-2,5'-bi-1,3-dioxane;

trans-5-butyl-trans-2'-(4-chloro-3,5-difluoro-phenethyl)-2,5'-bi-1,3-dioxane.

trans-2-(4-trifluoromethoxy-phenethyl)-5-[2-(trans-5-propyl-1,3-dioxan-2-yl)-ethyl]-1,3-dioxane;

trans-2-(4-trifluoromethoxy-phenethyl)-5-[2-(trans-5-butyl-1,3-dioxan-2-yl)-ethyl]-1,3-dioxane, m.p. (C-$S_B$) 103.4° C., cl.p. ($S_B$-I) 137.3° C.;

trans-2-(4-trifluoromethoxy-phenethyl)-5-[2-(trans-5-pentyl-1,3-dioxan-2-yl)-ethyl]-1,3-dioxane;

trans-2-(3,4-difluoro-phenethyl)-5-[2-(trans-5-propyl-1,3-dioxan-2-yl)-ethyl]-1,3-dioxane;

trans-2-(3,4-difluoro-phenethyl)-5-[2-(trans-5-butyl-1,3-dioxan-2-yl)-ethyl]-1,3-dioxane;

trans-2-(3,4-difluoro-phenethyl)-5-[2-(trans-5-pentyl-1,3-dioxan-2-yl)-ethyl]-1,3-dioxane;

(E)-trans-2-(3,4-difluoro-phenethyl)-5-[2-(trans-5-propenyl-1,3-dioxan-2-yl)-ethyl]-1,3-dioxane;

(E)-trans-2-(3,4-difluoro-phenethyl)-5-[2-(trans-5-but-1-enyl-1,3-dioxan-2-yl)-ethyl]-1,3-dioxane, m.p. (C-$S_B$) 99.6° C., cl.p. ($S_B$-I) 105.7° C.;

trans-2-(4-difluoromethoxy-3-fluoro-phenethyl)-5-[2-(trans-5-propyl-1,3-dioxan-2-yl)-ethyl]-1,3-dioxane;

trans-2-(4-difluoromethoxy-3-fluoro-phenethyl)-5-[2-(trans-5-butyl-1,3-dioxan-2-yl)-ethyl]-1,3-dioxane;

trans-2-(4-difluoromethoxy-3-fluoro-phenethyl)-5-[2-(trans-5-pentyl-1,3-dioxan-2-yl)-ethyl]-1,3-dioxane;

trans-2-(3,4,5-trifluoro-phenethyl)-5-[2-(trans-5-propyl-1,3-dioxan-2-yl)-ethyl]1,3-dioxane;

trans-2-(3,4,5-trifluoro-phenethyl)-5-[2-(trans-5-butyl-1,3-dioxan-2-yl)-ethyl]1,3-dioxane;

trans-2-(3,4,5-trifluoro-phenethyl)-5-[2-(trans-5-pentyl-1,3-dioxan-2-yl)-ethyl]1,3-dioxane;

trans-2-(4-difluoromethoxy-3,5-difluoro-phenethyl)-5-[2-(trans-5-propyl-1,3-dioxan-2-yl)-ethyl]1,3-dioxane;

trans-2-(4-difluoromethoxy-3,5-difluoro-phenethyl)-5-[2-(trans-5-butyl-1,3-dioxan-2-yl)-ethyl]1,3-dioxane;

trans-2-(4-difluoromethoxy-3,5-difluoro-phenethyl)-5-[2-(trans-5-pentyl-1,3-dioxan-2-yl)-ethyl]1,3-dioxane.

EXAMPLE 5

Binary mixtures (BM) with 4-(trans-4-pentylcyclohexyl)-benzonitrile were prepared in order to investigate the properties of the compounds of formula I in mixtures. The threshold potential ($V_{10}$) and the response times ($t_{on}$ and $t_{off}$) were measured at 22° C. in a TN cell (low bias tilt) with a plate separation of 8 μm; the 2.5-fold value of the threshold potential was chosen as the operating voltage. The corresponding data for 4-(trans-4-pentylcyclohexyl)-benzonitrile are: cl.p. (N-I) 54.6° C., $V_{10}$=1.62 V, $t_{on}$=22 ms, $t_{off}$=42 ms, Δn=0.120.

BM-1

90 wt. % of 4-(trans-4-pentylcyclohexyl)-benzonitrile 10 wt. % of trans-2-propyl-5-[2-(trans-5-propyl-1,3-dioxan-2-yl)-ethyl]-1,3-dioxane cl.p. (N-I) 46.2° C., $V_{10}$=1.43 V, $t_{on}$=30 ms, $t_{off}$=45 ms, Δn=0.105.

BM-2

80 wt. % of 4-(trans-4-pentylcyclohexyl)-benzonitrile 20 wt. % of trans-2-propyl-5-[2-(trans-5-propyl-1,3-dioxan-2-yl)-ethyl]-1,3-dioxane cl.p. (N-I) 38.2° C., $V_{10}$=1.29 V, $t_{on}$=36 ms, $t_{off}$=63 ms, Δn=0.096.

BM-3

90 wt. % of 4-(trans-4-pentylcyclohexyl)-benzonitrile 10 wt. % of trans-2-propyl-5-[2-(trans-5-pentyl-1,3-dioxan-2-yl)-ethyl]-1,3-dioxane cl.p. (N-I) 48.0° C., $V_{10}$=1.38 V, $t_{on}$=34 ms, $t_{off}$=51 ms, Δn=0.104.

BM-4

80 wt. % of 4-(trans-4-pentylcyclohexyl)-benzonitrile 20 wt. % of trans-2-propyl-5-[2-(trans-5-pentyl-1,3-dioxan-2-yl)-ethyl]-1,3-dioxane cl.p. (N-I) 42.2° C., $V_{10}$=1.31 V, $t_{on}$=43 ms, $t_{off}$=65 ms, Δn=0.098.

BM-5

90 wt. % of 4-(trans-4-pentylcyclohexyl)-benzonitrile 10 wt. % of (E)-trans-2-propyl-5-[2-(trans-5-propenyl-1,3-dioxan-2-yl)-ethyl]-1,3-dioxane cl.p. (N-I) 46.4° C., $V_{10}$=1.46 V, $t_{on}$=30 ms, $t_{off}$=51 ms.

BM-6

80 wt. % of 4-(trans-4-pentylcyclohexyl)-benzonitrile 20 wt. % of (E)-trans-2-propyl-5-[2-(trans-5-propenyl-1,3-dioxan-2-yl)-ethyl]-1,3-dioxane cl.p. (N-I) 39.4° C., $V_{10}$=1.32 V, $t_{on}$=37 ms, $t_{off}$=63 ms.

BM-7

90 wt. % of 4-(trans-4-pentylcyclohexyl)-benzonitrile 10 wt. % of trans-2-(trans-4-butylcyclohexyl)-5-[2-(trans-5-pentyl-1,3-dioxan-2-yl)-ethyl]-1,3-dioxane cl.p. (N-I) 58.6° C., $V_{10}$=1.62 V, $t_{on}$=29 ms, $t_{off}$=49 ms.

BM-8

90 wt. % of 4-(trans-4-pentylcyclohexyl)-benzonitrile 10 wt. % of trans-2-(3,4-difluorophenyl)-5-[2-(trans-5-propyl-1,3-dioxan-2-yl)-ethyl]-1,3-dioxane cl.p. (N-I) 51.3° C., $V_{10}$=1.46 V, $t_{on}$=30 ms, $t_{off}$=49 ms, Δn=0.116.

BM-9

80 wt. % of 4-(trans-4-pentylcyclohexyl)-benzonitrile 20 wt. % of trans-2-(3,4-difluorophenyl)-5-[2-(trans-5-propyl-1,3-dioxan-2-yl)-ethyl]-1,3-dioxane cl.p. (N-I) 49.0° C., $V_{10}$=1.28 V, $t_{on}$=40 ms, $t_{off}$=67 ms, Δn=0114.

BM-10

90 wt. % of 4-(trans-4-pentylcyclohexyl)-benzonitrile 10 wt. % of (E)-trans-2-(3,4-difluorophenyl)-5-[2-(trans-5-propenyl-1,3-dioxan-2-yl)-ethyl]-1,3-dioxane cl.p. (N-I) 52.1° C., $V_{10}$=1.46 V, $t_{on}$=30 ms, $t_{off}$=51 ms, Δn=0.117.

BM-11

90 wt. % of 4-(trans-4-pentylcyclohexyl)-benzonitrile 10 wt. % of trans-2-(3,4,5-trifluorophenyl)-5-[2-(trans-5-propyl-1,3-dioxane-2-yl)-ethyl]-1,3-dioxane cl.p. (N-I) 49.2° C., $V_{10}$=1.37 V, $t_{on}$=32 ms, $t_{off}$=52 ms, Δn=0.113.

BM-12

90 wt. % of 4-(trans-4-pentylcyclohexyl)-benzonitrile 10 wt. % of (E)-trans-2-(3,4,5-trifluorophenyl)-5-[2-(trans-5-propenyl-1,3-dioxan-2-yl)-ethyl]-1,3-dioxane cl.p. (N-I) 50.0° C., $V_{10}$=1.38 V, $t_{on}$=31 ms, $t_{off}$=53 ms, Δn=0.115.

We claim:

1. A compound of the formula

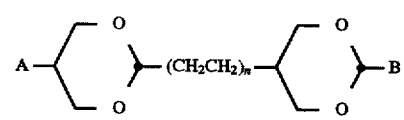

wherein

A and B each independently are cyclic or acyclic hydrophobic residues; and n is 0, 1 or 2.

2. A compound according to claim 1, wherein A and B are independently,

—R¹,

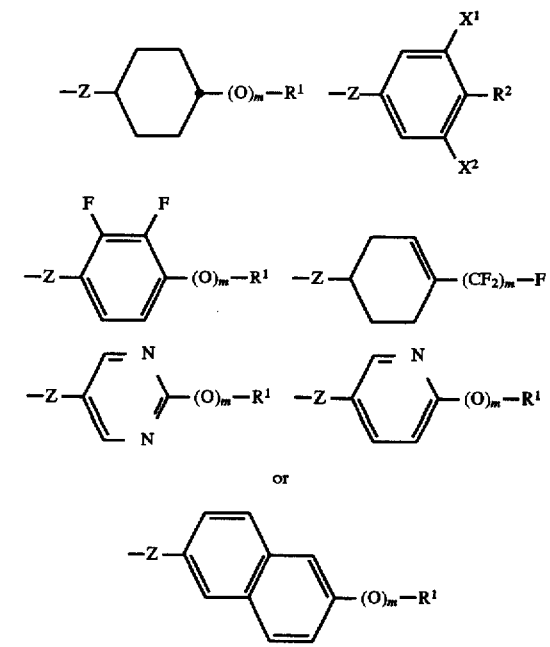

or

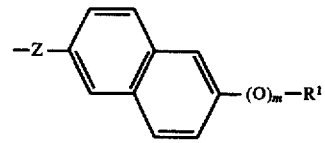

in which

Z is a single bond —CH₂CH₂— or —(CH₂)₄—;

X¹ and X² each independently are hydrogen or fluorine;

is 0 or 1;

R¹ is alkyl, alkenyl or alkoxyalkyl which is unsubstituted or substituted with at least one fluorine or chlorine atom; and R² is R¹, —O—R¹, fluorine, chlorine, cyano or isothiocyanato.

3. A compound according to claim 1 of the formulas

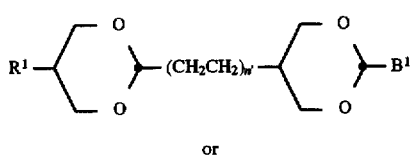
I-A or

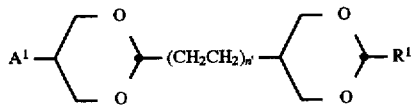
I-B wherein n' is 0 or 1;

R¹ is alkyl, alkenyl, or alkoxyalkyl which is unsubstituted or substituted with at least one fluorine or chlorine atom;

A¹ is alkyl, alkenyl, alkoxyalkyl or a group of the formula

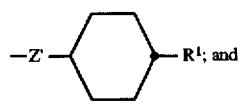

B¹ is alkyl, alkenyl, alkoxyalkyl or a group of the formula

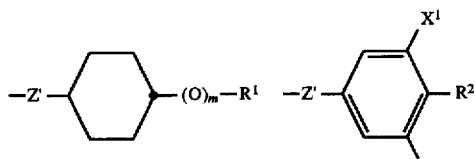

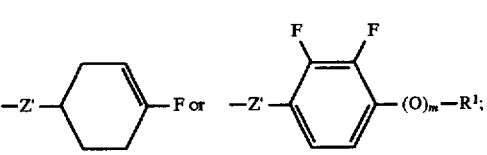

wherein m is 0 or 1;

Z' is a single bond or —CH$_2$CH$_2$—;

R¹ is alkyl, alkenyl, or alkoxyalkyl which is unsubstituted or substituted with at least one fluorine or chlorine atom;

R² is —O—R¹, fluorine, chlorine, cyano or isothiocyanato; and

X¹, X² each independently are hydrogen or fluorine.

4. A compound according to claim 3 of the formulas

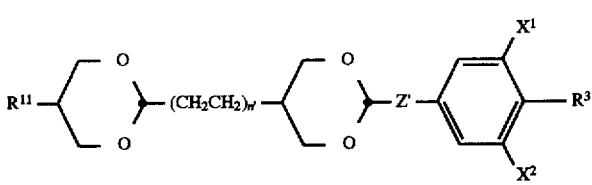
I-A1

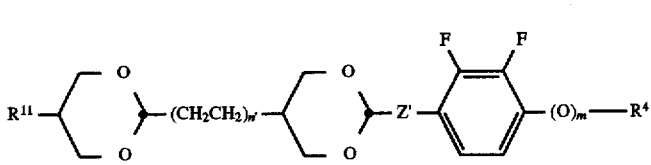
I-A2

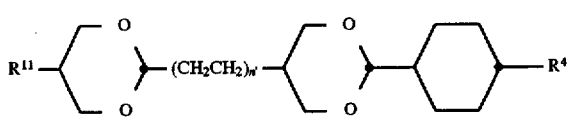
I-A3

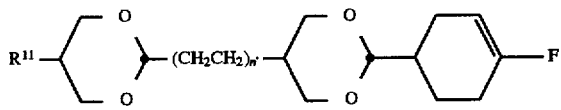
I-A4

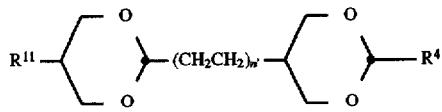
I-A5 wherein

R$^{11}$ is C$_1$-C$_7$ alkyl or C$_2$-C$_7$ alkenyl;
n' is 0 or 1;
m is 0 or 1;
X$^1$ and X$^2$ each independently are hydrogen or fluorine;
Z' is a single bond or —CH$_2$CH$_2$—;
R$^3$ is alkoxy, difluoromethoxy, trifluoromethoxy, chlorodifluoromethoxy, 2,2,2-trifluoroethyloxy, fluorine, chlorine or cyano; and
R$^4$ is C$_1$-C$_7$ alkyl, C$_2$-C$_7$ alkoxyalkyl or C2-C7 alkenyl.

5. A compound according to claim 3 of the formulas

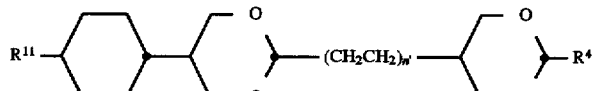

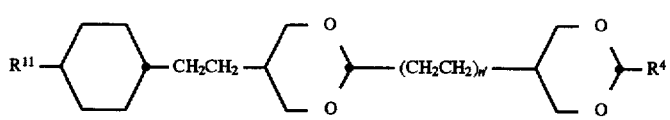

R$^{11}$ is C$_1$-C$_7$ alkyl or C$_2$-C$_7$ alkenyl;
n' is 0 or 1; and
R$^4$ is C$_1$-C$_7$ alkyl, C$_2$-C$_7$ alkoxyalkyl or C$_2$-C$_7$ alkenyl.

6. A compound according to claim 4 of the formula

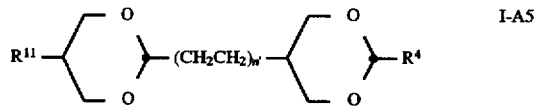

wherein n' is 1.

7. A compound according to claim 6, trans-2-ethyl-5-[2-(trans-5-propyl-1,3-dioxan-2-yl)-ethyl]-1,3-dioxane, trans-2-ethyl-5-[2-(trans-5-pentyl-1,3-dioxan-2-yl)-ethyl]-1,3-dioxane, trans-2-propyl-5-[2-(trans-5-propyl-1,3-dioxan-2-yl)-ethyl]-1,3-dioxane trans-2-propyl-5-[2-(trans-5-butyl-1,3-dioxan-2-yl)-ethyl]-1,3-dioxane, trans-2-propyl-5-[2-(trans-5-pentyl-1,3-dioxan-2-yl)-ethyl]-1,3-dioxane (E)-trans-2-ethyl-5-[2-(trans-5-propenyl-1,3-dioxan-2-yl)-ethyl]-1,3-dioxane, (E)-trans-2-propyl-5-[2-(trans-5-propenyl-1,3-dioxan-2-yl)-ethyl]-1,3-dioxane, or (E)-trans-2-propyl-5-[2-(trans-5-but-1-enyl-1,3-dioxan-2-yl)-ethyl]-1,3-dioxane.

8. A compound according to claim 4 of the formula

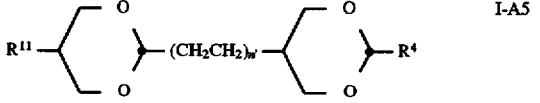

wherein n' is 0.

9. A compound according to claim 8, trans-2-butyl-5-(trans-5-propyl-1,3-dioxan-2-yl)-1,3-dioxane, trans-2-butyl-5-(trans-5-butyl-1,3-dioxan-2-yl)-1,3-dioxane, trans-2-butyl-5-(trans-5-pentyl-1,3-dioxan-2-yl)-1,3-dioxane, (E)-trans-2-butyl-5-(trans-5-propenyl-1,3-dioxan-2-yl)-1,3-dioxane, (E)-trans-2-butyl-5-(trans-5-but-1-enyl-1,3-dioxan-2-yl)-1,3-dioxane, trans-5-butyl-trans-2'-propyl-2,5'-bi-1,3-dioxane, trans,trans-5,2'-dipropyl-2,5'-bi-1,3-dioxane, or trans,trans-5,2'-dipentyl-2,5'-bi-1,3-dioxane.

10. A compound according to claim 4 of the formula

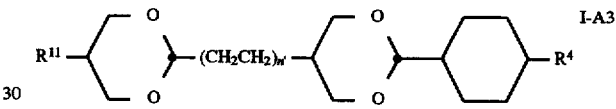

wherein n' is 1.

11. A compound according to claim 10, trans-2-(trans-4-butylcyclohexyl)-5-[2-(trans-5-propyl-1,3-dioxan-2-yl)-ethyl]-1,3-dioxane, trans-2-(trans-4-butylcyclohexyl)-5-[2-(trans-5-butyl-1,3-dioxan-2-yl)-ethyl]-1,3-dioxane, trans-2-(trans-4-butylcyclohexyl)-5-[2-(trans-5-pentyl-1,3-dioxan-2-yl)-ethyl]-1,3-dioxane (E)-trans-2-(trans-4-butylcyclohexyl)-5-[2-(trans-5-propenyl-1,3-dioxan-2-yl)-ethyl]-1,3-dioxane, or (E)-trans-2-(trans-4-butylcyclohexyl)-5-[2-(trans-5-but-1- enyl-1,3-dioxan-2-yl)-ethyl]-1,3-dioxane.

12. A compound according to claim 4 of the formula

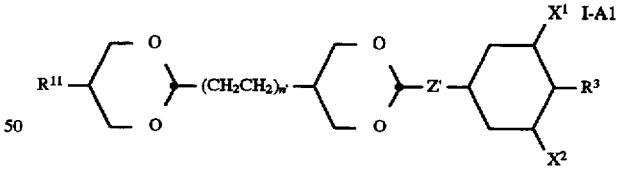

wherein n'=1 and Z' is a single bond.

13. A compound according to claim 12, trans-2-(3,4-difluorophenyl)-5-[2-(trans-5-propyl-1,3-dioxan-2-yl)-ethyl]-1,3-dioxane trans-2-(3,4-difluorophenyl)-5-[2-(trans-5-butyl-1,3-dioxan-2-yl)-ethyl]-1,3dioxane, (E)-trans-2-(3,4-difluorophenyl)-5-[2-(trans-5-propenyl-1,3-dioxan-2-yl)-ethyl]-1,3-dioxane trans-2-(3,4,5-trifluorophenyl)-5-[2-(trans-5-propyl-1,3-dioxan-2-yl)-ethyl]-1,3-dioxane (E)-trans-2-(3,4,5-trifluorophenyl)-5-[2-(trans-5-propenyl-1,3-dioxan-2-yl)-ethyl]-1,3-dioxane trans-2-(4-trifluoromethyl-phenyl)-5-[2-(trans-5-propyl-1,3-dioxan-2-yl)-ethyl]-1,3-dioxane, trans-2-(4-trifluoromethyl-phenyl)-5-[2-(trans-5-butyl-1,3-dioxan-2-yl)-ethyl]-1,3-dioxane, or (E)-trans-2-(4-trifluoromethyl-phenyl)-5-[2-(trans-5-propenyl-1,3-dioxan-2-yl)-ethyl]-1,3-dioxane.

14. A compound according to claim 4 of the formula

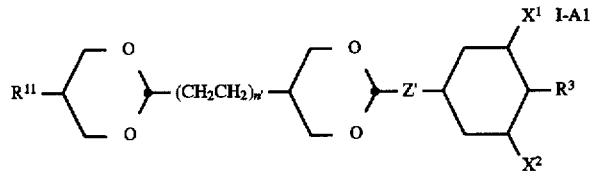

wherein n'=1 and Z' is —CH$_2$CH$_2$—.

15. A compound according to claim 14, trans-2-(4-trifluoromethoxy-phenethyl)-5-[2-(trans-5-butyl-1,3-dioxan-2-yl)-ethyl]-1,3-dioxane, or (E)-trans-2-(3,4-difluorophenethyl)-5-[2-(trans-5-but-1-enyl-1,3-dioxan-2-yl)-ethyl]-1,3-dioxane.

16. A compound according to claim 4 of the formula

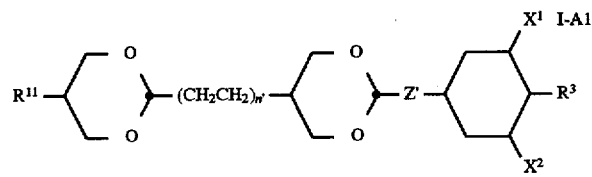

wherein n'=0 and Z' is a single bond.

17. A compound according to claim 16, trans-5-propyl-trans-2'-(4-trifluoromethyl-phenyl)-2,5'-bi-1,3-dioxane, trans-5-butyl-trans-2'-(4-trifluoromethyl-phenyl)-2,5'-bi-1,3-dioxane, trans-5-pentyl-trans-2'-(4-trifluoromethyl-phenyl)-2,5'-bi-1,3-dioxane, trans-5-propyl-trans-2'-(4-trifluoromethoxy-phenyl)-2,5'-bi-1,3-dioxane, trans-5-butyl-trans-2'-(4-trifluoromethoxy-phenyl)-2,5'-bi-1,3-dioxane, trans-5-pentyl-trans-2'-(4-trifluoromethoxy-phenyl)-2,5'-bi-1,3-dioxane, trans-5-propyl-trans-2'-(3,4-difluoro-phenyl)-2,5'-bi-1,3-dioxane trans-5-butyl-trans-2'-(3,4-difluoro-phenyl)-2,5'-bi-1,3-dioxane, trans-5-pentyl-trans-2'-(3,4-difluoro-phenyl)-2,5'-bi-1,3-dioxane, trans-5-propyl-trans-2'-(3,4,5-trifluoro-phenyl)-2,5'-bi-1,3-dioxane, trans-5-butyl-trans-2'-(3,4,5-trifluoro-phenyl)-2,5'-bi-1,3-dioxane, or trans-5-pentyl-trans-2'-(3,4,5-trifluoro-phenyl)-2,5'-bi-1,3-dioxane.

18. A compound according to claim 4 of the formula

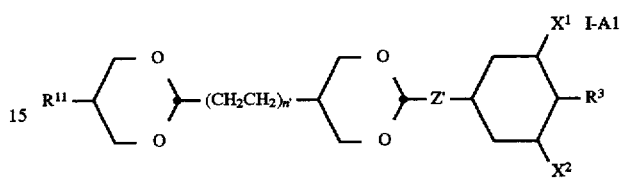

wherein n'=0 and Z' is —CH$_2$CH$_2$—.

19. A compound according to claim 18, trans-2'-(3,4-difluoro-phenethyl)-trans-5-butyl-2,5'-bi-1,3-dioxane, trans-5-butyl-trans-2'-(4-trifluoromethyl-phenethyl)-2,5'-bi-1,3-dioxane, trans-5-butyl-trans-2'-(3,4-difluoro-phenethyl)-2,5'-bi-1,3-dioxane, or trans-5-pentyl-trans-2'-(3,4-difluoro-phenethyl)-2,5'-bi-1,3-dioxane.

20. A liquid crystalline mixture having at least 2 components, wherein at least one component is a compound of the formula

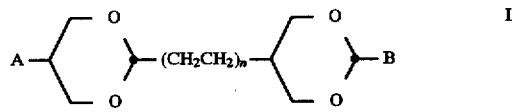

wherein

A and B each independently are cyclic or acyclic hydrophobic residues; and n is 0, 1 or 2.

21. A liquid crystalline mixture according to claim 20, wherein the content of compounds of formula 1 is 1–30 wt. %.

* * * * *